(12) United States Patent
Thomas et al.

(10) Patent No.: US 10,271,557 B2
(45) Date of Patent: Apr. 30, 2019

(54) COMPOSITION COMPRISING A BACTERIOCIN AND AN EXTRACT FROM A PLANT OF THE LABIATAE FAMILY

(71) Applicant: DUPONT NUTRITION BIOSCIENCES APS, Copenkagen K (DK)

(72) Inventors: Linda V Thomas, South Ruislip (GB); Richard Ingram, Beaminster (GB); Torben Isak, Hinnerup (DK); Bob Coyne, Lenexa, KS (US); John Faragher, Milwaukee, WI (US); Sebastien Gouin, Arhus (DK); Carsten Bjoern Hansen, Ega (DK); Kathryn Louise Tse, Copenhagen (DK)

(73) Assignee: DUPONT NUTRITION BIOSCIENCES APS (DK)

( * ) Notice: Subject to any disclaimer, the term of this patent is extended or adjusted under 35 U.S.C. 154(b) by 429 days.

(21) Appl. No.: 14/974,437

(22) Filed: Dec. 18, 2015

(65) Prior Publication Data

US 2016/0100588 A1   Apr. 14, 2016

Related U.S. Application Data

(63) Continuation of application No. 10/568,324, filed as application No. PCT/GB2004/003423 on Aug. 6, (Continued)

(30) Foreign Application Priority Data

Aug. 22, 2003 (GB) .................................. 0319817.3
Oct. 6, 2003 (GB) .................................. 0323335.0

(51) Int. Cl.
| | | |
|---|---|---|
| A01N 65/22 | (2009.01) | |
| A21D 2/00 | (2006.01) | |
| A23B 4/10 | (2006.01) | |
| A23B 4/12 | (2006.01) | |
| A23B 4/20 | (2006.01) | |
| A23B 4/22 | (2006.01) | |
| A23B 5/06 | (2006.01) | |
| A23B 5/14 | (2006.01) | |
| A23B 5/16 | (2006.01) | |
| A23C 19/084 | (2006.01) | |
| A23C 19/11 | (2006.01) | |
| A23L 2/52 | (2006.01) | |
| A23L 3/3463 | (2006.01) | |
| A23L 3/3472 | (2006.01) | |
| A23L 3/3544 | (2006.01) | |
| A23L 3/3571 | (2006.01) | |
| B01J 13/04 | (2006.01) | |
| B01J 13/08 | (2006.01) | |
| B01J 13/14 | (2006.01) | |
| B01J 13/22 | (2006.01) | |
| A01N 31/08 | (2006.01) | |

(Continued)

(52) U.S. Cl.
CPC ............. *A01N 65/22* (2013.01); *A01N 25/28* (2013.01); *A01N 31/08* (2013.01); *A01N 35/06* (2013.01); *A01N 37/36* (2013.01); *A01N 37/38* (2013.01); *A01N 37/46* (2013.01); *A21D 2/00* (2013.01); *A23B 4/10* (2013.01); *A23B 4/12* (2013.01); *A23B 4/20* (2013.01); *A23B 4/22* (2013.01); *A23B 5/06* (2013.01); *A23B 5/14* (2013.01); *A23B 5/16* (2013.01); *A23C 19/084* (2013.01); *A23C 19/11* (2013.01); *A23L 2/52* (2013.01); *A23L 3/3472* (2013.01); *A23L 3/34635* (2013.01); *A23L 3/3544* (2013.01); *A23L 3/3571* (2013.01); *A23L 13/72* (2016.08); *A23L 33/127* (2016.08); *A23L 33/135* (2016.08); *A23P 10/30* (2016.08); *A23P 10/35* (2016.08); *B01J 13/043* (2013.01); *B01J 13/08* (2013.01); *B01J 13/14* (2013.01); *B01J 13/22* (2013.01); *A23V 2002/00* (2013.01); *Y10T 428/2984* (2015.01)

(58) Field of Classification Search
None
See application file for complete search history.

(56) References Cited

U.S. PATENT DOCUMENTS 3,187,019 A   6/1965 Jeffries
3,576,759 A   4/1971 Powell et al.
(Continued)

FOREIGN PATENT DOCUMENTS

CH      509098 A    6/1971
CN      1334181     2/2002
(Continued)

OTHER PUBLICATIONS

Karatzas et al., J. Applied Microbiology, 2000, vol. 89, p. 296-301.
(Continued)

*Primary Examiner* — Terry A McKelvey
*Assistant Examiner* — Catheryne Chen

(57) ABSTRACT

The present invention provides a composition comprising (a) an antimicrobial material; and (b) an extract obtained from or obtainable from a plant of the Labiatae family, wherein (a) and (b) are different; wherein the composition contains phenolic diterpenes in an amount of greater than 1.0 wt. %, based on the composition, and wherein when the antimicrobial material consists of nisin, the composition comprises carvacrol in an amount of less than 0.075 wt. % based on the composition and carvone in an amount of less than 15 wt. % based on the composition.

20 Claims, 11 Drawing Sheets

Related U.S. Application Data 2004, now abandoned, which is a continuation-in-part of application No. 10/820,147, filed on Apr. 8, 2004, now abandoned.

(60) Provisional application No. 60/497,409, filed on Aug. 22, 2003, provisional application No. 60/533,053, filed on Dec. 30, 2003, provisional application No. 60/560,270, filed on Apr. 8, 2004.

(51) Int. Cl.
| | |
|---|---|
| A01N 35/06 | (2006.01) |
| A01N 37/36 | (2006.01) |
| A01N 37/38 | (2006.01) |
| A01N 37/46 | (2006.01) |
| A01N 25/28 | (2006.01) |
| A23P 10/30 | (2016.01) |
| A23P 10/35 | (2016.01) |
| A23L 33/10 | (2016.01) |
| A23L 33/135 | (2016.01) |
| A23L 13/70 | (2016.01) |

(56) References Cited

U.S. PATENT DOCUMENTS

| | | | |
|---|---|---|---|
| 3,679,434 | A | 7/1972 | Bard et al. |
| 5,032,404 | A | 7/1991 | Lopez-Berestein et al. |
| 5,084,293 | A | 1/1992 | Todd |
| 5,139,787 | A | 8/1992 | Broderick et al. |
| 5,204,029 | A | 4/1993 | Morgan et al. |
| 5,215,757 | A | 6/1993 | El-Nokaly |
| 5,445,949 | A | 8/1995 | Koster et al. |
| 5,472,684 | A | 12/1995 | Nabi et al. |
| 5,516,543 | A | 5/1996 | Amankonah et al. |
| 5,580,573 | A | 12/1996 | Kydonieus et al. |
| 5,738,888 | A | 4/1998 | Cirigliano et al. |
| 5,780,056 | A | 7/1998 | Akamatsu et al. |
| 5,821,233 | A | 10/1998 | Van et al. |
| 5,895,680 | A | 4/1999 | Cirigliano et al. |
| 5,997,926 | A | 12/1999 | Van et al. |
| 6,033,705 | A | 3/2000 | Isaacs |
| 6,083,921 | A | 7/2000 | Xu |
| 6,126,974 | A | 10/2000 | Ang |
| 6,207,210 | B1 | 3/2001 | Bender et al. |
| 6,294,192 | B1 | 9/2001 | Patel et al. |
| 6,312,741 | B1 | 11/2001 | Navarro |
| 6,375,968 | B1 | 4/2002 | Quong |
| 6,451,365 | B1 | 9/2002 | King et al. |
| 6,500,463 | B1 | 12/2002 | Van Lengerich |
| 6,673,756 | B2 | 1/2004 | Sonnenberg et al. |
| 6,723,358 | B1 | 4/2004 | Van Lengerich |
| 7,090,882 | B2 | 8/2006 | Koefod et al. |
| 2002/0061954 | A1 | 5/2002 | Davis et al. |
| 2002/0173436 | A1 | 11/2002 | Sonnenberg et al. |
| 2002/0192352 | A1 | 12/2002 | Dar |
| 2003/0108648 | A1 | 6/2003 | Ming et al. |
| 2004/0018284 | A1 | 1/2004 | Kuethe et al. |
| 2004/0109927 | A1 | 6/2004 | Ang et al. |
| 2004/0253352 | A1 | 12/2004 | Koefod et al. |
| 2005/0067726 | A1 | 3/2005 | Yan et al. |

FOREIGN PATENT DOCUMENTS

| | | |
|---|---|---|
| EP | 0770336 A1 | 5/1997 |
| EP | 0687417 B1 | 12/1998 |
| EP | 1157618 A1 | 11/2001 |
| EP | 1369045 A2 | 12/2003 |
| EP | 1382261 A1 | 1/2004 |
| GB | 2275194 A | 8/1994 |
| GB | 2388581 A | 11/2003 |
| JP | 2257866 A | 10/1990 |
| JP | H03500051 A | 1/1991 |
| JP | 7039355 A | 2/1995 |
| JP | 7039356 A | 2/1995 |
| JP | 2001172159 A | 6/2001 |
| JP | 2001299304 | 10/2001 |
| RU | 2099087 | 12/1997 |
| RU | 2158587 | 10/2000 |
| WO | 8701587 A1 | 3/1987 |
| WO | 89/03208 A1 | 4/1989 |
| WO | 8912399 A1 | 12/1989 |
| WO | 9114445 A1 | 10/1991 |
| WO | 9608248 A1 | 3/1996 |
| WO | 9747289 A1 | 12/1997 |
| WO | 9856395 A1 | 12/1998 |
| WO | 0030631 A1 | 6/2000 |
| WO | 0042987 A2 | 7/2000 |
| WO | 0122972 A3 | 4/2001 |
| WO | 0130326 A1 | 5/2001 |
| WO | 02055043 A1 | 7/2002 |
| WO | 02069741 A1 | 9/2002 |
| WO | 02094224 A1 | 11/2002 |
| WO | 2004041251 A1 | 5/2004 |

OTHER PUBLICATIONS

Krasaekoopt W et al, International Dairy Journal; vol. 13; No. 1; pp. 3-13 (2003).
Lante A et al, Biotechnology Letters; vol. 16; No. 3; pp. 293-298 (1994).
Lante et al, Industrie Alimentari, 2000, "Nisin released from membrane reactor for dairy Clostridia control"; vol. 39, No. 392, p. 589-595.
Laridi et al, International Dairy Journal; vol. 13; No. 4, p. 325-336; (2003) ISSN: 0958-6946 & Database BIOSIS accession No. PREV200300195252 XP002301927.
Lipstock et al "Toxicity of intravitral rifampin" Medical College of Virginia—Virginia Commonwealth University (abstract only), Investigative Ophthalmology and Visual Science, 1981, vol. 20, No. 2, No. 3 suppl. p109.
MacNeil et al, Journal of Food Science; vol. 38; pp. 1080-1081 (1973).
MacNeil, Frankfurters without Nitrates or Nitrites; Food Product Development, 1973, pp. 36-40.
Moujir L et al, Phytochemistry; vol. 34; No. 6; pp. 1493-1495 (1993).
Munne-Bosch S et al, Eur. Food Res. Technol., 2000, vol. 210, p. 263-267.
Munne-Bosch S et al, Plant Physiol., 2001, vol. 125, No. 2 p. 1094-1102.
Nychas G, "Natural antimicrobials from Plants"; New Methods of Food Preservation (ed G W Gould), Blackie Academic, London, Chapter 4, pp. 58-89.
Ol I E et al, Letters in Applied Microbiology; vol. 29; 1999; pp. 166-170.
Olasupo N A et al, Letters in Applied Microbiology, 2003, vol. 36, p. 448-451 XP009037915.
Pandit V A et al, Food Microbiology 1994, vol. 11, p. 57-63.
Parmar V S et al, Indian Journal of Chemistry, 1996, vol. 35B, p. 220-232.
Periago M et al, Food Science and Technology International, 2001, vol. 7, No. 6, 487-492.
Periago P M et al, International Journal of Food Microbiology, 2001, vol. 68, p. 141-148.
Pol I E et al, Innovative Food Science & Emerging Technologies, 2002, vol. 3, p. 55-61.
Pol I E et al, Letters in Applied Microbiology, 1999, vol. 29, p. 166-170.
Pol I E et al., "Improved applicability of nisin in novel combinations with other food preservation factors", Thesis, Danisco (2001) ISBN 90-5808-382-9.
Powell J et al, "Sensory and analytical analysis of milk formulations with sweet cream buttermilk", Virginia Polytechnic Institute and State University (abstract only).
Quirin K W, Innovations in Food Technology, 2003, vol. 81, p. 31-33 (abstract only).

(56) References Cited

OTHER PUBLICATIONS

Ranum, P., 1999. "Encapsulated mold inhibitors—the greatest thing since sliced bread", Cereal Foods World, vol. 44, No. 5, p. 370-371.
Richard et al., "Use of bacteriocin producing starters advantageously in dairy industry" INRA, Dairy Research Unit.
Rose N et al, Journal of Food Science; vol. 67; No. 6; pp. 2288-2293 (2002).
Rose N L et al, Journal of Food Science, 1999, vol. 64, No. 5, p. 759-762.
Sagdic et al "Antibacterial activity of Turkish spice hydrosols", Food Source Control (2003) vol. 14:3 pp. 141-143 (abstract only).
Salim A et al, Food and Chemical Toxicology, 2003, vol. 41, p. 595-597.
Schlyter J H et al, International Journal of Food Microbiology, 1993, vol. 19, p. 271-281.
Serra B J et al, Journal of the science of Food and agriculture, 2003, vol. 83, No. 4 p. 275-282.
Shahidi F et al, Critical Reviews in Food Science and Nutrition; vol. 33; No. 6; pp. 501-547 (1993).
Sidikaro et al "Concentration of gentamicin in preocular tear film following topical application" Cullen Eye Institute, Baylor College of Medicine, Houston, Texas (abstract only).
Spillane S M et al., "Antimicrobial effect of nisin-containing microspheres", Chemical Abstract, 2000, 134:2512 CA, Proceed. International, Symp. Control. Rel. Bioact. Mater., 2000, vol. 27, p. 1373-1374.
Stecher P, 1968, The Merck Index, 8th edition, Merck & Co Inc, Rahway, New Jersey, p. 971.
Sundararajan et al, "Inactivation of nisin by alpha-chymotrypsin", The Journal of Dairy Science, 1969, vol. 52, vol. 9, p. 1448-1450.
Talcott S T et al, Journal of Agriculture and Food Chemistry, 2003, vol. 51, No. 4, p. 957-963.
Taylor S L et al, Journal of Food Protection; vol. 48; No. 11; pp. 949-952 (1985).
Thaiudom S. et al., "Rheological properties of primary stabilizer/ milk protein/κ-carrageenan/sucrose systems simulating ice cream mix", Journal of Dairy Science, 2001, vol. 84, No. 1 suppl. p. 382 XP002301925 abstract 1583.
Thaludom et al Rheological properties of primary stabilizer/milk protein/ carageenlsucrose systems simulating ice cream mix University of Guelph, Guelph, ON Canada (abstract only).
Thomas L V et al, Journal of Applied Microbiology, 1998, vol. 85, p. 1013-1022.
Usborne W R et al, Canadian Institute of Food Science and Tech.; vol. 19; No. 1; pp. 38-40 (1986).
Valero et al, International Journal of Food Microbiology; vol. 85; pp. 73-81; (2003).
Walker "Antimicrobial compounds in food plants" Department of Plant and Microbial Sciences, University of Canterbury. pp. 181-200.
Wan J et al, Journal of Applied Bacteriology; vol. 79; pp. 671-676; (1995).
Wan J et al, Letters in Applied Microbiology vol. 24; pp. 153-158; (1997).
Were et al, Database Medline 'Online!'; US National Library of Medicine (NLM), May 2004; "Encapsulation of nisin and lysizym in liposomes enhances . . . ", Database Accession No. NLM15151228 & Journal of Food Protection, May 2004, vol. 67, No. 5,pp. 922-927.
WPI Abstract Acc. No. 1995-117843[16] & JP 7039355 A.
WPI Abstract Acc. No. 2001-599861[68] & JP 2001172159 A.
Yang et al., Bioorganic & Medicinal Chemistry, 2001, vol. 9, p. 347-356.
Alves Virginal Farias et al, "Bacteriocin exposure and food ingredients influence on growth and virulence of listeria monocytogenes in a model meat gravy system", Journal of Food Safety, 2003, vol. 23, p. 201-217.
Aureli P et al, Journal of Food Protection; vol. 55; No. 5; pp. 344-348; (1992).
Backleh M et al, Journal of Agricultural and Food Chemistry, 2003, vol. 51, No. 5, p. 1297-1301 (abstract only).
Basaga et al, Food Science and Technology—Lebensmittel Wissenschaft & Technologies; vol. 30; No. 1; p. 105-108; (1997).
Bell PG et al, Food Microbiology, 1987, vol. 4, p. 277-283.
Belmont et al "Pimaricin: corneal penetration via a liposome vehicle" Francis I Proctor Foundation, University of California San Francisco (abstract only).
Benech R-O et al, Applied and Environmental Microbiology, Aug. 2002, p. 3683-3690 XP002301922.
Beuchat, Antimicrobial Properties of Spices and Their Essential Oils; in Natural Antimicrobial systems and food preservation, eds V M Dillon and R G Board, CAB International, 1994, pp. 167-179.
Bicchi et al., Phytochemical Analysis, 2000, vol. 11, p. 236-242.
Bower C K et al, Applied and Environmental Microbiology; vol. 61; No. 3; pp. 992-997 (1995).
Bower C K et al, Journal of Industrial Microbiology vol. 15; pp. 227-233 (1995).
Cahill et al, in Durieuix A and Simon J-P (eds) Applied Microbiology; pp. 239-266 (2001).
Calucci L et al, Journal of Agricultural and Food Chemistry, 2003, vol. 51, No. 4, p. 927-934 (abstract only).
Campbell W et al, Journal of Dairy Science (2003) vol. 86:1 pp. 43-51 (abstract only).
Casterio et al, Industrial Alimentari, 1979, p. 1-12.
Clark J P, Food Encapsulation; Capturing One Substance by Another; Products & Technologies, vol. 56; No. 11; p. 63-65 (2002).
Collins et al, Food Microbiology; vol. 4; pp. 311-315; (1987).
Cutter C N et al, Food Microbiology; vol. 14; pp. 425-430; (1997).
Cutter C N et al, Letters in Applied Microbiology; vol. 23; pp. 9-12 (1996).
Cutter C N et al, Letters in Applied Microbiology; vol. 27; pp. 19-23 (1998).
Cutter CN et al, Food Microbiology, 1997, vol. 14, p. 425-430.
Cutter et al, Letters in Applied Microbiology; vol. 23; pp. 9-12 (1996).
Cuvelier et al, JAOCS; vol. 73; No. 5; pp. 645-653; (1996).
Daeschel M A, Journal of Food Protection; vol. 55; No. 9; pp. 731-735 (1992).
Database Biosis 'Online!', Biosciences Information Service, Philadelphia, Laridi et al; "Liposome encapsulated nisin Z . . . "; Database Accession No. PREV200300195252 & International Dairy Journal, vol. 13, No. 4 pp. 325-336 XP0022301927.
Database Caplus; Chemical Abstracts Service, Columbus: "Pharmaceutical liposomes containing . . . " Database Accession No. 115:263475 XP002301928 & U.S. Pat. No. 5,032,404.
Degnan A J et al, International Journal of Food Microbiology, 1993, vol. 18, p. 127-138 XP002301924.
Del Campo J et al, Journal of Food Protection, vol. 63; No. 10; pp. 1359-1368; (2000).
Dougherty et al "Chronic blepharitis: new perspectives" University of Texas Health Science Centre at Dallas, Texas (abstract only).
Dufour M et al, International Journal of Food Microbiology, 2000, vol. 85, p. 249-258.
Eiserle R J, Food Product Development (1971) pp. 70-71.
Etayebi K et al, FEMS Microbiology Letters; vol. 183, 2000, p. 191-195 XP002300239.
Fang T J et al, Food Microbiology vol. 20; pp. 243-253 (2003).
Farbood M I et al, J. Milk Food Technol; vol. 39; No. 10; pp. 675-679; (1976).
Francis, Frederick J. , Food Science and Technology, 2nd edition, vol. 1, John Wiley & Sons, Inc, New York, p. 68-69.
Francis, Frederick J. , Food Science and Technology, 2nd edition, vol. 1, John Wiley & Sons, Inc, New York, p. 65.
Zaika, Spices and Herbs; Journal of Food Safety; vol. 9; pp. 97-118; (1988).
Frankel E N et al, Journal of Agricultural Food Chemistry; vol. 44; pp. 131-135; (1996).
Franklin et al "Consumer evaluation of "high-CLA dairy products" produced from cows fed fish oil" University of Kentucky, Lexington, KY (abstract only).
FSRIO—Agricultural Research Service, National Program 108, Food Safety Progress Report 2002.

(56) References Cited

OTHER PUBLICATIONS

Gallagher G A et al, Food Safety Progress Report, 2002.
Gola J, Science and Research in the Food Industry, 1962, vol. 10, p. 239-244.
Imm et al "Control of acidification of yoghurt by microencapsulated bacteriocin" Korean Food Research Institute, Korea Yakult Co., Ltd., Korea University (abstract only).
International Food Abstracts—Science and Technology; (May 2003) pp. 1-5.
Izco et al "Use of capillary electrophoresis (CE) to determine metabolic organic acids in milk" Dairy Products technology Centre, Cal. Poly. (abstract only).
Jaben et al "Intraocular miconazole therapy in fungal endopithalmitis" Department of ophthalmology, Bascom Palmer Eye Institute, University of Miami School of Medicine (abstract only).
Jung D S, The Journal of Dairy Science; 1992, vol. 75; pp. 387-393.
Kabara J J et al, Journal of Food Safety, 1982, vol. 4, p. 13-25.
Kabara J J, Antimisobials in Food Eats PM Davidson & Albranen ed. Marcel Dekker (1993) pp. 307-342.
Kane et al "Intravitreal Injection of Gentamicin in Rabbits" New England Medical Center Hospital and Tufts University School of Medicine, Boston (abstract only).
Wong et al., "Release characteristics of pectin microspheres prepared by an emulsification technique," J. Microencapsulation, 2002, vol. 19, No. 4, pp. 511-522.
Were et al., "Encapsulation of nisin and lysozyme in liposomes enhances efficacy against Listeria monocytogenes," Journal of Food Protection, 2004, vol. 67, pp. 922-927.
U.S. Appl. No. 10/765,210, filed Jan. 28, 2004.
Thomas et al. "Natamycin," Danisco Technical Paper, 2003, pp. 4009-4115.
Stark, "Natamycin," Chapter 9, Food Preservatives, 2nd Edition, 2003, Kluwer Academic / Plenum Publishers, New York, NY, pp. 179-195 (Book Not Included).
Sanghvi et al., "Effect of viscosity and interfacial tension on particle size of cellulose acetate trimellitate microspheres," Journal of Microencapsulation, 1991, vol. 9, No. 2, pp. 215-227.
Ranum, "Encapsulated mold-inhibitors—the greatest thing since sliced bread?," Cereal Foods World, May 1999, vol. 44, No. 5, pp. 370-371.
PCT International Search Report for Application No. PCT/GB2004/003423; Molina de Alba, J., Authorized Officer; ISA/EPO, Nov. 18, 2004.
Mofidi et al., "Mass preparation and characterization of alginate microspheres," Process Biochemistry, 2000, vol. 35, pp. 885-888.
MacNeil, "Frankfurters without nitrates or nitrites," Food Product Development Mar. 1973, pp. 37-40.
Lipstock et al., "Toxicity intravitral rifampin," Investigative Ophthalmology and Visual Science, 1981, vol. 20, No. 2, No. 3 Suppl., pp. 109, Medical College of Virginia—Virginia Commonwealth University (Abstract).
Lee et al., "Whey Protein-based Microcapsules Prepared by Double Emulsification and Heat Gelation," Lebensm.-Wiss. U.-Technol, Mar. 2000, vol. 33, No. 2, pp. 80-88.
Laridi et al., "Liposome encapsulated nisin Z: optimization, stability and release during milk fermentation," International Dairy Journal, 2003, vol. 13. pp. 325-336.
Lante et al., "Il controllo di clostridi di interesse caseario con nisina immobilizzata in membrance semipermeabili," Industrie Alimentari, 2000, pp. 589-594.
Koontz et al., "Stability of Natamycin and Its Cyclodextrin Inclusion Complexes in Aqueous Solution," L Agric. Food Chem., 2003, vol. 51, No. 24, pp. 7111-7114.
Koontz et al, "Formation of Natamycin: Cyclodextrin Inclusion Complexes and Their Characterization," Journal of Agricultural and Food Chemistry, 2003, vol. 51, pp. 7106-7110.
Frankel et al., "Antioxidant Activity of a Rosemary Extract and Its Constituents, Carnosic Acid, Carnosol, and Rosmarinic Acid, in Bulk Oil and Oil-in-Water Emulsion," Journal of Agricultural and Food Chemistry, 1996, vol. 44, No. 1, pp. 131-135.
Dinsmore et al., "Colloidosomes: Selectively Permeable Capsules Composed of Colloidal Particles," Science, Nov. 1, 2001, vol. 298, pp. 1006-1009.
Degnam et al., "Influence of Beef Tallow and Muscle on the Antilisterial Activity of Pediocin AcH and Liposome-Encapsulated Pediocin AcH," Journal of Food Protection, Jul. 1992, vol. 55, No. 7, pp. 552-554.
Basaga et al., "Antioxidative and Free Radical Scavenging Properties of Rosemary Extract" Lebensm.-Wiss. U-Technol., 1997, vol. 30, Academic Press Limited, pp. 105-108.
"Microencapsulation," Kirk-Othmer Encyclonedia of Chemical Technology, 3rd Edition, Ed., vol. 15, pp. 473-474 (Book Not Included).

COMPOSITION COMPRISING A BACTERIOCIN AND AN EXTRACT FROM A PLANT OF THE LABIATAE FAMILY

CROSS-REFERENCE TO RELATED PATENT APPLICATIONS

This patent claims priority as a continuation under 35 U.S.C. § 120 to U.S. patent application Ser. No. 10/568,324 (filed Oct. 13, 2006 and published on May 10, 2007 as US Patent Appl. Publ. No. US2007/0104809 on May 10, 2007), which, in turn, claims priority under 35 USC § 371 as a national phase of Int'l Patent Appl. PCT/GB2004/003423 (filed Aug. 6, 2004; and published on Mar. 3, 2005 as Int'l Publ. No. WO2005/018333), which, in turn, claims priority to GB Patent Appl. No. 0319817.3 (filed Aug. 22, 2003); U.S. Prov. Patent Appl. No. 60/497,409 (filed Aug. 22, 2003); GB Patent Appl. No. 0323335.0 (filed Oct. 6, 2003); U.S. Prov. Patent Appl. No. 60/533,053 (filed Dec. 30, 2003); and U.S. Prov. Patent Appl. No. 60/560,270 (filed Apr. 8, 2004); and as a continuation-in-part under 35 U.S.C. § 120 to U.S. patent application Ser. No. 10/820,147 (filed Apr. 8, 2004 and published on Feb. 24, 2005 as US Patent Appl. Publ. No. US2005/0042341), which, in turn, claims priority to GB Patent Appl. No. 0319817.3 (cited above) and U.S. Prov. Patent Appl. No. 60/497,409 (cited above). The entire texts of the above-referenced patent applications are incorporated by reference into this patent.

The present invention relates to a composition that exhibits a microbicidal or microbiostatic action.

BACKGROUND

Bacteriocins are antimicrobial proteins or peptides that can be produced by certain bacteria, which can kill or inhibit the growth of closely related bacteria. The bacteriocins produced by lactic acid bacteria are of particular importance since they have great potential for the preservation of food and for the control of foodborne pathogens. (Wessels et al. 1998.)

The most well known bacteriocin is nisin, which is the only bacteriocin currently authorised as a food additive. Nisin is produced by fermentation of the dairy starter culture bacterium *Lactococcus lactis* subsp. *lactis*, and is sold as the commercial extract NISAPLIN® Natural Antimicrobial (Danisco). Nisin has an unusually broad antimicrobial spectrum for a bacteriocin, being active against most Gram-positive bacteria (e.g. species of *Bacillus, Clostridium, Listeria*, lactic acid bacteria). It is not normally effective against Gram-negative bacteria, yeasts or moulds. Nisin is allowed as a food preservative worldwide but its levels of use and approved food applications are strictly regulated, varying from country to country.

Other bacteriocins have since been discovered with potential as food preservatives, e.g. pediocin, lacticin, sakacin, lactococcin, enterococin, plantaricin, leucocin. These are also active, although usually with a more narrow spectrum, against Gram-positive bacteria. Their food use is at present restricted to production of the bacteriocin in situ, i.e. by growth of the producer organism within the food.

Antioxidants are widely used in food products susceptible to oxidative degeneration. An antioxidant is defined by the Food and Drug Administration (21CFR 170.3) as "a substance used to preserve food by retarding deterioration, rancidity, or discoloration due to oxidation". Spices or plant extracts can be used in food as antioxidants and to impart flavour. One advantage of such extracts is that they are perceived as natural ingredients when compared to chemical antioxidants such as butyl hydroxyanisol (BHA) and butylated hydoxytoluene (BHT). Plants of the family Labiatae contain several well known herbs. Extracts from these plants have been shown to have antioxidant and, in some cases, antimicrobial activity (Nychas & Skandamis, 2003; Smid and Gorris, 1999; Loliger, 1989). Such extracts may be essential oils and oleoresins (extracts with essential oil content used in flavours and fragrances) or "deodorised'", extracts that have a high phenolic diterpene content and low level of flavour-inducing compounds.

Essential oils are extracted by simple steam distillation of the plant material. The most effective antioxidant compounds in rosemary and sage are reported to be carnosic acid, camosol and rosmarinic acid (Cuvelier et al. 1996). Carnosic acid, a phenolic diterpene ($C_{20}H_{28}O_4$), occurs naturally in leaves of plants of the Labiatae family, particularly rosemary and sage, but also thyme and marjoram. Dried leaves of rosemary or sage contain 1.5-2.5% carnosic acid and 0.3-0.4% camosol (U.S. Pat. No. 6,231,896). Camosol is an oxidative artefact of carnosic acid (Wenkert et al. J. Org. Chem 30:2931, 1965). The oxidation takes place in the presence of harvesting in the leaves left to dry in the air and if the leaves are subjected to extraction with solvents. Rosmanol may also be a product of the oxidation of carnosic acid.

The use of extracts of plant material for inhibiting the growth of micro-organisms has been taught in the art. Examples of such teachings include: WO 02/069741 teaches Labiatae herb extracts and hop extracts for extending the colour lie and inhibiting the growth of micro-organisms in fresh meat, fish and poultry. Periago et al. 2001. Food Science & Technology International. 7: 487-492 relates to the use of Carvacrol and thymol at 0.3 mmol/liter in combination with nisin. It is taught that synergy is observed. JP 2001172159 relates to cosmetics comprising a range of components including antimicrobial agent and Labiatae solvent extract. WO 98/56395 teaches a mix of tea-tree oil and thyme Essential oil. GB 2275 194 A discusses plant extract disinfectant. U.S. Pat. No. 6,083,921 discusses a combination of plant extracts including one from Labiatae: *Scutellaria*, preferably root (*Radix scutellariae*). U.S. Pat. No. 5,472,684 teaches an oral composition for plaque and gingivitis containing thymol and eugenol Food safety and prevention of food spoilage is an ever present concern worldwide, particularly with the increasing trend for convenience foods such as ready to eat meals, soups, sauces or snacks. Spoilage of food is a major economic problem for the food manufacturer. Food manufacturers need to protect the health and safety of the public by delivering products that are safe to eat. Such food must have a guaranteed shelf life, either at chilled or ambient temperature storage. Consumers prefer good tasting food of high quality—this is difficult to achieve with chemical preservatives, harsh heating regimes and other processing measures. Food safety and protection is best achieved with a multiple preservation system using a combined approach of milder processing and natural preservatives. Foodborne microorganisms are also less able to adapt and grow in food preserved with different preservative measures.

There is much concern about food safety and the growth of food pathogens such as *Listeria monocytogenes*. This particular pathogen can grow at low temperatures, which are often used as an additional preservative measure. Foodborne pathogens can sometimes adapt to different preservatives and storage conditions, thus a combination of preservative measures can be more successful than individual measures.

There is an increasing need to develop economical, natural and effective food preservative systems to meet the public demand for convenient, natural, safe, healthy, good quality food products with guaranteed shelf life. Bacteriocins such as nisin can be used as preservatives in food to help meet this need. Nisin is a proven safe, natural preservative with GRAS status. Other bacteriocins can be used for preservation if produced in situ, by growth of the bacteriocin producer organism in the food.

In some cases the bacteriocin levels required to ensure preservation or food safety may prove uneconomical, or are below effective levels due to regulatory and legislation constraints. When bacteriocins are produced in situ, the resulting bacteriocin levels may not be high enough to achieve the required preservative effect.

The present invention alleviates the problems of the prior art.

In one aspect the present invention provides a composition comprising (a) an antimicrobial material; and (b) an extract obtained from or obtainable from a plant of the Labiatae family, wherein (a) and (b) are different wherein the composition contains phenolic diterpenes in an amount of greater than 1.0 wt. %, based on the composition, and wherein when the antimicrobial material consists of nisin, the composition comprises carvacrol in an amount of less than 0.075 wt. % based on the composition and carvone in an amount of less than 15 wt. % based on the composition.

In one aspect the present invention provides a process for preventing and/or inhibiting the growth of, and/or killing a micro-organism in a material, the process comprising the step of contacting the material with (a) an antimicrobial material; and (b) an extract obtained from or obtainable from a plant of the Labiatae family, wherein (a) and (b) are different; wherein the composition contains phenolic diterpenes in an amount of greater than 1.0 wt. %, based on the composition, and wherein when the antimicrobial material consists of nisin, the composition comprises carvacrol in an amount of less than 0.075 wt. % based on the composition and carvone in an amount of less than 15 wt. % based on the composition.

In one aspect the present invention provides use of (a) an antimicrobial material; and b) an extract obtained from or obtainable from a plant of the Labiatae family, for preventing and/or inhibiting the growth of, and/or killing a micro-organism in a material; wherein (a) and (b) are different; wherein the composition contains phenolic diterpenes in an amount of greater than 1.0 wt. %, based on the composition, and wherein when the antimicrobial material consists of nisin, the composition comprises carvacrol in an amount of less than 0.075 wt. % based on the composition and carvone in an amount of less than 15 wt. % based on the composition.

In one aspect the present invention provides kit for preparing a composition as defined herein, the kit comprising (a) an antimicrobial material; and (b) an extract obtained from or obtainable from a plant of the Labiatae family, wherein (a) and (b) are different; wherein the composition contains phenolic diterpenes in an amount of greater than 1.0 wt. %, based on the composition, and wherein when the antimicrobial material consists of nisin, the composition comprises carvacrol in an amount of less than 0.075 wt. % based on the composition and carvone in an amount of less than 15 wt. % based on the composition, in separate packages or containers; optionally with instructions for admixture and/or contacting and/or use.

Aspects of the invention are defined in the appended claims.

Of the Labiatae plant family, rosemary and sage have antioxidant activity in foods that is mainly related to phenolic diterpenes such as camosic acid and camosol, as well as other phenolic compounds, including phenolic triterpenes such as betulinic acid, oleanolic acid and ursolic acid; and rosmarinic acid. Antimicrobial activity has been attributed to some of these compounds, all of which can be obtained by selective extraction from the plants. The phenolic diterpenes, phenolic triterpenes and rosmarinic acid are distinct from the essential oils and oleoresins that are often used in flavours and fragrances. The high flavour and odour levels of essential oils is not conducive to their use in food. One skilled in the art would expect a combination of an antimicrobial material and an extract from the Labiatae plant family to provide a simple additive bactericidal or bacteriostatic effect. However, in vitro studies described herein have demonstrated synergistic enhancement of bacteriocin activity by a deodorised extract of *Rosmarinus officinalis*. This enhanced activity was also observed in a food model, increasing bacteriocin (for example nisin) kill and growth control of Gram-positive bacteria. Enhanced bacteriocin activity was also observed with rosemary extracts specifically prepared to contain high levels of the phenolic diterpenes camosol and camosic acid, indicating these compounds play an important role in the synergy. Enhanced bacteriocin activity was also observed with rosmarinic acid.

The present invention provides a synergistic combination of components for preventing and/or inhibiting the growth of, and/or killing a micro-organism in a material, such as foodstuff. This combination of components allows lower levels of the antimicrobial material to be used to provide effective action and prevent the development of tolerance to the antimicrobial material. This is particularly important in food applications where reduction of dosage and/or avoidance of development of tolerance is desired for commercial and regulatory reasons.

For ease of reference, these and further aspects of the present invention are now discussed under appropriate section headings. However, the teachings under each section are not necessarily limited to each particular section.

Preferred Aspects
Antimicrobial Material

In one preferred aspect the antimicrobial material is a bacteriocin.

The antimicrobial material, such as a bacteriocin, may typically be selected from materials (bacteriocins) that can be used as preservatives in food Preferably the antimicrobial material is selected from lanthionine containing bacteriocins, *Lactococcus*-derived bacteriocins, *Streptococcus*-derived bacteriocins, *Pediococcus*-derived bacteriocins, *Lactobacillus*-derived bacteriocins, *Camobacterium*-derived bacteriocins, *Leuconostoc*-derived bacteriocins, *Enterococcus*-derived bacteriocins and mixtures thereof Preferably the antimicrobial material is at least nisin.
Preferably the antimicrobial material consists of nisin.
Nisin is a lanthionine-containing bacteriocin (U.S. Pat. No. 5,691,301) derived from *Lactococcus lactis* subsp. *lactis* (formerly known as *Streptococcus-lactis*) (U.S. Pat. No. 5,573,801). In a preferred aspect of the present invention the bacteriocin used in the present invention is at least nisin.

As discussed in U.S. Pat. No. 5,573,801 nisin is a polypeptide bacteriocin produced by the lactic acid bacteria, *Lactococcus lactis* subsp. *lactis* (formerly known as *Streptococcus lactis* Group N).

Nisin is reportedly a collective name representing several closely related substances which have been designated nisin compounds A, B, C, D and E (De Vuyst, L. and Vandamme, E. J. 1994. Nisin, a lantibiotic produced by *Lactococcus lactis* subsp. *lactis*: properties, biosynthesis, fermentation and applications. In: Bacteriocins of lactic acid bacteria. Microbiology, Genetics and Applications. Eds.: De Vuyst and Vandamme. Blackie Academic and Professional, London). The structure and properties of nisin are also discussed in the article by E. Lipinska, entitled "Nisin and Its Applications", The 25th Proceedings of the Easter School in Agriculture Science at the University of Nottingham, 1976, pp. 103-130 (1977), which article is hereby incorporated by reference. In 1969 the FAO/WHO Joint Expert Committee on Food Additives set specifications for the purity and identity of nisin (FAO/WHO Joint Expert Committee on Food Additives. 1969. Specifications for identity and purity of some antibiotics. $12^{th}$ Report. WHO Technical Report Series No. 430). This committee recognised nisin as a safe and legal preservative based on extensive toxicological testing. Nisin has the food additive number E234 and is classed as GRAS (Generally Recognised As Safe) (Food and Drug Administration. 1988. Nisin preparation: Affirmation of GRAS status as a direct human ingredient. Federal Regulations 53: 11247). The international activity unit (IU hereinafter) was defined as 0.001 mg of an international nisin reference preparation. NISAPLIN® Natural Antimicrobial is the brand name for a nisin concentrate containing 1 million IU per g, which is commercially available from Danisco.

Nisin is an acknowledged and accepted food preservative with a long history of safe, effective food use. There have been several reviews of nisin, e.g. Hurst 1981; 1983; Delves-Broughton, 1990; De Vuyst and Vandamme, 1994; Thomas et al. 2000; Thomas & Delves-Broughton, 2001). Nisin was discovered over 50 years ago and the first commercial preparation, made in 1953, was NISAPLIN®. Nisin has several characteristics that make it particularly suitable as a food preservative. It has undergone extensive toxicological testing to demonstrate its safety. It is heat-stable, acid-stable and effective against a broad spectrum of Gram-positive bacteria. It is not normally effective against Gram-negative bacteria, yeasts or moulds but activity against Gram-negative bacteria and yeasts has been reported in the presence of chelating agents (PCT/US 8902625. WO 89/12399). Nisin is an effective preservative in pasteurised and heat-treated foods (e.g. processed cheese, cheese, pasteurised milks, dairy desserts, cream, mascarpone and other dairy products, puddings such as semolina, tapioca etc., pasteurised liquid egg, pasteurised potato products, soy products, crumpets, pikelets, flapjacks, processed meat products, beverages, soups, sauces, ready to eat meals, canned foods, vegetable drinks) and low acid foods such as salad dressings, sauces, mayonnaise, beer, wine and other beverages.

Although some loss of activity may be expected when used with processed foods, this may be ameliorated e.g. by increasing the amount of nisin applied. Effective levels of nisin to preserve foodstuffs reportedly range from 25-500 IU/g or more. Other effective levels would be appreciated by one skilled in the art. For example levels of 50-400 IU/g may be utilised.

Since the discovery of the first bacteriocin, nisin, many other bacteriocins have now been found (Hoover, 1993; Ray & Daeschel, 1994; Axelsen, 1998; Naidu, 2000; Ray at al. 2001; Ray & Miller, 2003). The bacteriocin pediocin, produced by *Pediococcus pentosaceus, P. acidilactici*, or *Lactobacillus plantarum*, may be used in the present invention. Like nisin, different structures of pediocin have been described. At present pediocin and other bacteriocins are not allowed as food additives but their antibacterial activity can be achieved by production of the bacteriocin in situ, as a consequence of the growth of the producer organism in the food. This is the purpose of commercial protective cultures such as HOLDBAC™ *Listeria* (Danisco). Pediocin has a more narrow antimicrobial spectrum compared to nisin, but there is much interest in its food safety ability to kill, prevent or control the growth of the food pathogen *Listeria monocytogenes* (Ray & Miller, 2000). Other bacteriocins may be used in the present invention, including those named generally as divercin, leucctcin, mesentericin, sakacin, curvacin, bavaricin, acidocin, bifidocin, camobacteriocin, pisicocin, piscicolin, mundticin, enterocin, thermophilin, lacticin, plantaricin, lactococcin, divercin, diplococcin, mesenterocin, leuconosin, camosin, acidophilin, lactacin, brevicin, lactocin, helevticin, reutericin, propionicin.

Extract

As discussed herein when the antimicrobial material consists of nisin, the composition comprises carvacrol in an amount of less than 0.075 wt. % based on the composition and carvone in an amount of less than 15 wt. % based on the composition.

In one preferred aspect when the antimicrobial material consists of nisin, the composition comprises carvacrol in an amount of less than 0.05 wt. % based on the composition, preferably less than 0.04 wt. %, preferably less than 0.02 wt. %, preferably less than 0.01 wt. %, preferably less than 0.004 wt. %, based on the composition.

In one preferred aspect, the composition comprises carvacrol in an amount of less than 0.05 wt. % based on the composition, preferably less than 0.04 wt. %, preferably less than 0.02 wt. %, preferably less than 0.01 wt. %, preferably less than 0.004 wt. %, based on the composition.

In one preferred aspect when the antimicrobial material consists of nisin, the composition comprises carvone in an amount of less than 10 wt. % based on the composition, preferably less than 7 wt. %, preferably less than 5 wt. %, preferably less than 2 wt. %, preferably less than 1 wt. %, preferably less than 0.75 wt. %, preferably less than 0.5 wt. %, preferably less than 0.2 wt. %, preferably less than 0.1 wt. %, preferably less than 0.075 wt. %, preferably less than 0.05 wt. %, preferably less than 0.04 wt. %, preferably less than 0.02 wt. %, preferably less than 0.01 wt. %, preferably less than 0.004 wt. %, based on the composition.

In one preferred aspect the composition comprises carvone in an amount of less than 10 wt. % based on the composition, preferably less than 7 wt. %, preferably less than 5 wt. %, preferably less than 2 wt. %, preferably less than 1 wt. %, preferably less than 0.75 wt. %, preferably less than 0.5 wt. %, preferably less than 0.2 wt. %, preferably less than 0.1 wt. %, preferably less than 0.75 wt. %, preferably less than 0.05 wt. %, preferably less than 0.04 wt. %, preferably less than 0.02 wt. %, preferably less than 0.01 wt. %, preferably less than 0.004 wt. %, based on the composition.

In one preferred aspect when the antimicrobial material consists of nisin, the composition comprises thymol in an amount of less than 15 wt. % based on the composition, preferably less than 10 wt. %, preferably less than 7 wt. %, preferably less than 5 wt. %, preferably less than 2 wt. %, preferably less than 1 wt. %, preferably less than 0.75 wt. %, preferably less than 0.5 wt. %, preferably less than 0.2 wt. %, preferably less than 0.1 wt. %, preferably less than 0.075 wt. %, preferably less than 0.05 wt. %, preferably less than 0.04 wt. %, preferably less than 0.02 wt. %, preferably less than 0.01 wt. %, preferably less than 0.004 wt. %, based on the composition.

In one preferred aspect the composition comprises thymol in an amount of less than 15 wt. % based on the composition preferably less than 10 wt. %, preferably less than 7 wt. %, preferably less than 5 wt. %, preferably less than 2 wt. %, preferably less than 1 wt. %, preferably less than 0.75 wt. %, preferably less than 0.5 wt. %, preferably less than 0.2 wt. %, preferably less than 0.1 wt. %, preferably less than 0.075 wt. %, preferably less than 0.05 wt. %, preferably less than 0.04 wt. %, preferably less than 0.02 wt. %, preferably less than 0.01 wt. %, preferably less than 0.004 wt. %, preferably less than 0.004 wt. %, based on the composition.

In one preferred aspect when the antimicrobial material consists of nisin, the composition comprises eugenol in an amount of less than 15 wt. % based on the composition, preferably less than 10 wt. %, preferably less than 7 wt. %, preferably less than 5 wt. %, preferably less than 2 wt. %, preferably less than 1 wt. %, preferably less than 0.75 wt. %, preferably less than 0.5 wt. %, preferably less than 0.2 wt. %, preferably less than 0.1 wt. %, preferably less than 0.075 wt. %, preferably less than 0.05 wt. %, preferably less than 0.04 wt. %, preferably less than 0.02 wt. %, preferably less than 0.01 wt. %, preferably less than 0.004 wt. %, based on the composition.

In one preferred aspect the composition comprises eugenol in an amount of less than 15 wt. % based on the composition preferably less than 10 wt. %, preferably less than 7 wt. %, preferably less than 5 wt. %, preferably less than 2 wt. %, preferably less than 1 wt. %, preferably less than 0.75 wt. %, preferably less than 0.5 wt. %, preferably less than 0.2 wt. %, preferably less than 0.1 wt. %, preferably less than 0.075 wt. %, preferably less than 0.05 wt. %, preferably less than 0.04 wt. %, preferably less than 0.02 wt. %, preferably less than 0.01 wt. %, preferably less than 0.004 wt. %, based on the composition.

In one preferred aspect when the antimicrobial material consists of nisin, the composition comprises carvacrol in an amount of less than 0.075 wt. % based on the composition and each of carvone and thymol in amounts of less than 15 wt. % based on the composition (preferably less than 10 wt. % based on the composition, preferably less than 7 wt. %, preferably less than 5 wt. %, preferably less than 2 wt. %, preferably less than 1 wt. %, preferably less than 0.75 wt. %, preferably less than 0.5 wt. %, preferably less than 0.2 wt. %, preferably less than 0.1 wt. %, preferably less than 0.075 wt. %, preferably less than 0.05 wt. %, preferably less than 0.04 wt. %, preferably less than 0.02 wt. %, preferably less than 0.01 wt. %, preferably less than 0.004 wt. %, based on the composition).

In one preferred aspect, the composition comprises carvacrol in an amount of less than 0.075 wt. % based on the composition and each of carvone and thymol in amounts of less than 15 wt. % based on the composition (preferably less than 10 wt. % based on the composition, preferably less than 7 wt. %, preferably less than 5 wt. %, preferably less than 2 wt. %, preferably less than 1 wt. %, preferably less than 0.75 wt. %, preferably less than 0.5 wt. %, preferably less than 0.2 wt. %, preferably less than 0.1 wt. %, preferably less than 0.075 wt. %, preferably less than 0.05 wt. %, preferably less than 0.04 wt. %, preferably less than 0.02 wt. %, preferably less than 0.01 wt. %, preferably less than 0.004 wt. %, based on the composition).

In one preferred aspect when the antimicrobial material consists of nisin, the composition comprises carvacrol in an amount of less than 0.075 wt. % based on the composition and each of carvone, thymol and eugenol in amounts of less than 15 wt. % based on the composition (preferably less than 10 wt. % based on the composition, preferably less than 7 wt. %, preferably less than 5 wt. %, preferably less than 2 wt. %, preferably less than 1 wt. %, preferably less than 0.75 wt. %, preferably less than 0.5 wt. %, preferably less than 0.2 wt. %, preferably less than 0.1 wt. %, preferably less than 0.075 wt. %, preferably less than 0.05 wt. %, preferably less than 0.04 wt. %, preferably less than 0.02 wt. %, preferably less than 0.01 wt. %, preferably less than 0.004 wt. %, based on the composition).

In one preferred aspect, the composition comprises carvacrol in an amount of less than 0.075 wt. % based on the composition and each of carvone, thymol and eugenol in amounts of less than 15 wt. % based on the composition (preferably less than 10 wt. % based on the composition, preferably less than 7 wt. %, preferably less than 5 wt. %, preferably less than 2 wt. %, preferably less than 1 wt. %, preferably less than 0.75 wt. %, preferably less than 0.5 wt. %, preferably less than 0.2 wt. %, preferably less than 0.1 wt. %, preferably less than 0.075 wt. %, preferably less than 0.05 wt. %, preferably less than 0.04 wt. %, preferably less than 0.02 wt. %, preferably less than 0.01 wt. %, preferably less than 0.004 wt. %, based on the composition).

In one preferred aspect when the antimicrobial material consists of nisin, the composition comprises each of carvacrol and carvone in an amount of less than 1 wt. % based on the extract. Preferably when the antimicrobial material consists of nisin the composition comprises each of carvacrol and carvone in an amount of less than 0.075 wt. %, preferably less than 0.05 wt. %, preferably less than 0.04 wt. %, preferably less than 0.02 wt. %, preferably less than 0.01 wt. %, preferably less than 0.004 wt. %, based on the extract.

In one preferred aspect when the antimicrobial material consists of nisin, the composition comprises each of carvacrol, carvone and thymol in amounts of less than 1 wt. % based on the extract. Preferably when the antimicrobial material consists of nisin the composition comprises each of carvacrol, carvone and thymol in an amount of less than 0.075 wt. %, preferably less than 0.05 wt. %, preferably less than 0.04 wt. %, preferably less than 0.02 wt. %, preferably less than 0.01 wt. %, preferably less than 0.004 wt. %, based on the extract.

In one preferred aspect when the antimicrobial material consists of nisin, the composition comprises each of carvacrol, carvone, thymol and eugenol in amounts of less than 1 wt. % based on the extract. Preferably when the antimicrobial material consists of nisin the composition comprises each of carvacrol, carvone, thymol and eugenol in an amount of less than 0.075 wt. %, preferably less than 0.05 wt. %, preferably less than 0.04 wt. %, preferably less than 0.02 wt. %, preferably less than 0.01%4.%, preferably less than 0.004 wt. %, based on the extract.

In one preferred aspect the composition comprises each of carvacrol and carvone in an amount of less than 1 wt. % based on the extract. Preferably the composition comprises each of carvacrol and carvone in an amount of less than 0.075 wt. %, preferably less than 0.05 wt. %, preferably less than 0.04 wt. %, preferably less than 0.02 wt. %, preferably less than 0.01 wt. %, preferably less than 0.004 wt. %, based on the extract.

In one preferred aspect the composition comprises each of carvacrol, carvone and thymol in amounts of less than 1 wt. % based on the extract. Preferably the composition comprises each of carvacrol, carvone and thymol in an amount of less than 0.075 wt. %, preferably less than 0.05 wt. %, preferably less than 0.04 wt. %, preferably less than 0.02 wt. %, preferably less than 0.01 wt. %, preferably less than 0.004 wt. %, based on the extract.

In one preferred aspect the composition comprises each of carvacrol, carvone, thymol and eugenol in amounts of less than 1 wt. % based on the extract. Preferably the composition comprises each of carvacrol, carvone, thymol and eugenol in an amount of less than 0.075 wt. %, preferably less than 0.05 wt. %, preferably less than 0.04 wt. %, preferably less than 0.02 wt. %, preferably less than 0.01 wt. %, preferably less than 0.004 wt. %, based on the extract.

The extract used in the present invention is obtained from or is obtainable from a plant of the Labiatae family.

In one aspect the extract used in the present invention is obtained from a plant of the Labiatae family.

It will be appreciated by one skilled in the art that by the term "extract" or "extracts" it is meant any constituent of the plant which may be isolated from the whole plant.

In one aspect the extract used in the present invention is obtainable from a plant of the Labiatae family. It will be appreciated by one skilled in the art that an extract obtainable from a plant may be obtained from a plant or may be isolated from the plant, identified and then obtained from an alternative source, for example by chemical synthesis or enzymatic production. For example the extract may be produced by a eukaryotic or prokaryotic fermentation, by a process of genetic manipulation. The present applicant have recognised that products present in a plant of the Labiatae family may synergistically increase the activity of a an antimicrobial material, preferably a bacteriocin. These products may be obtained from any source and will fall within the scope of the present invention.

The invention comprises use of a combination of a bacteriocin such as nisin and a of the Labiatae plant family, such as rosemary (*Rosmarinus officinalis*) or sage (*Salvia officinalis*) that together give enhanced control of Gram-positive bacteria in a food system. The extracts responsible for synergy in the present invention preferably refer to extracts of the plant family Labiatae that have been selectively extracted ("deodorised extracts") to increase their phenolic diterpene content (such as carnosol and camosic acid), phenolic triterpene content (such as ursolic acid, betulinic acid and oleanolic acid) or rosmarinic acid content. These deodorised extracts can be distinguished by their high phenolic diterpene content (for example greater than 3.5 wt. %) and their low level (less than 1 wt. %) of flavour-inducing compounds from plant essential oils and oleoresins that are used as flavours or fragrances. Essential oils are typically extracted by simple steam distillation of the plant material.

Essential oils comprise the various essential oils in plants having the odour or the flavour of the plant from which they were extracted. The essential oils are typically terpenoids often comprising monoterpenes. For example an antioxidant type of rosemary extract, which could be described as selectively extracted or deodorised, contains >3.5% phenolic diterpenes but less than 1 wt. % essential oils. A non-selective, flavouring extract contains 10-30 wt. % essential oils and a phenolic diterpene content of 2→3.5 wt. %.

An essential oil is commonly described as the volatile ethereal fraction obtained from a plant or plant part by a physical separation process such as distillation or chromatographic separation. Essential oils have also been described as a group of odorous principles, soluble in alcohol and to a limited extent in water, consisting of a mixtures of esters, aldehydes, ketones and terpenes. Essential oils are typically obtained by distilling plants with water, the oil that separates from distillate usually has highly characteristic odors identified with the plant origin. The resulting mixture of organic compounds was thought, in the days of alchemists, to be the essence of the plant, hence the term "essential oil".

In one preferred aspect the extract is a deodorised extract. Preferably the (deodorised) extract contains from 1.0 to 70 wt. % phenolic diterpenes, preferably 3.5 to 70 wt. % phenolic diterpenes and less than 1 wt. % essential oil.

In one preferred aspect the extract is selected from phenolic diterpenes, phenolic triterpenes and rosmarinic acid.

In one preferred aspect the extract is or comprises a phenolic diterpene. Preferably the phenolic diterpene is selected from carnosic acid, carnosol and methylcamosic acid. Preferably the phenolic diterpene is selected from camosic acid and carnosol.

In one preferred aspect the combined amount of phenolic diterpenes, and phenolic triterpenes and rosmarinic acid, based on the extract, is greater than 1.0 wt. %. In one preferred aspect the combined amount of phenolic diterpenes, and phenolic triterpenes and rosmarinic acid, based on the composition, is greater than 1.0 wt. %.

In one preferred aspect the combined amount of phenolic diterpenes, and phenolic triterpenes and rosmarinic acid, based on the extract, is greater than 3.5 wt. %. In one preferred aspect the combined amount of phenolic diterpenes, and phenolic triterpenes and rosmarinic acid, based on the composition, is greater than 3.5 wt. %.

In one preferred aspect the amount of phenolic diterpenes, based on the extract, is greater than 1.0 wt. %, for example greater than 5.0 wt. %, greater than 10.0 wt. %, greater than 20.0 wt. %, or greater than 25.0 wt. %. In one preferred aspect the amount of phenolic diterpenes, based on the composition, is greater than 1.0 wt. %.

In one preferred aspect the amount of phenolic diterpenes, based on the extract, is greater than 3.5 wt. %. In one preferred aspect the amount of phenolic diterpenes, based on the composition, is greater than 3.5 wt. %.

In one preferred aspect the amount of phenolic diterpenes, based on the composition, is greater than 1.0 wt. %, preferably greater than 2.0 wt. %, preferably greater than 3.0 wt. %, preferably greater than 3.5 wt. %, preferably greater than 5.0 wt. %, preferably greater than 10.0 wt. %, preferably greater than 20.0 wt. %, preferably greater than 40.0 wt. %, preferably greater than 50.0 wt. %.

In one preferred aspect the amount of phenolic diterpenes, based on the composition, is from 2.0 to 2.5 wt. %, such as 2.3 wt. %.

In one preferred aspect the amount of phenolic diterpenes, based on the composition, is from 4.0 to 4.5 wt. %, such as 4.2 wt. %.

In one preferred aspect the amount of phenolic diterpenes, based on the extract, is greater than 1.0 wt. %, preferably greater than 2.0 wt. %, preferably greater than 3.0 wt. %, preferably greater than 3.5 wt. %, preferably greater than 5.0 wt. %, preferably greater than 10.0 wt. %, preferably greater than 20.0 wt. %, preferably greater than 40.0 wt. %, preferably greater than 50.0 wt. %.

In one highly preferred aspect the extract contains one or more phenolic triterpenes. Preferably the phenolic triterpenes are selected from betulinic acid, oleanolic acid, and ursolic acid.

In one preferred aspect is or comprises a phenolic triterpene. Preferably the phenolic triterpene is selected from betulinic acid, oleanolic acid, and ursolic acid.

In one highly preferred aspect the amount of phenolic triterpenes, based on the extract, is greater than 3.5 wt. %. In one highly preferred aspect the amount of phenolic triterpenes, based on the composition, is greater than 3.5 wt. %.

In one preferred aspect the extract is or comprises rosmarinic acid.

In one preferred aspect the amount of rosmarinic acid, based on the extract, is greater than 3.5 wt. %. In one preferred aspect the amount of rosmarinic acid, based on the composition, is greater than 3.5 wt. %.

In one preferred aspect the extract contains flavour-inducing compounds and/or essential oils in an amount of less than 1 wt. % based on the extract. In one preferred aspect the extract contains flavour-inducing compounds and/or essential oils in an amount of less than 1 wt. % based on the composition.

Typically flavour-inducing compounds and/or essential oils are camphor, verbenone, borneol and alfa-terpineol.

In one preferred aspect the combined amount of camphor present in the extract is less than 1 wt. % (preferably less than 0.2 wt. %, more preferably less than 0.15 wt. %, more preferably less than 0.1 wt. %) based on the extract.

In one preferred aspect the combined amount of verbenone present in the extract is less than 1 wt. % (preferably less than 0.2 wt. %, more preferably less than 0.15 wt. %, more preferably less than 0.1 wt. %) based on the extract.

In one preferred aspect the combined amount of borneol present in the extract is less than 1 wt. % (preferably less than 0.2 wt. %, more preferably less than 0.15 wt. %, more preferably less than 0.1 wt. %) based on the extract.

In one preferred aspect the combined amount of alfa-terpineol present in the extract is less than 1 wt. % (preferably less than 0.2 wt. %, more preferably less than 0.15 wt. %, more preferably less than 0.1 wt. %) based on the extract.

In one preferred aspect the combined amount of camphor, verbenone, borneol and alfa-terpineol present in the extract is less than 1 wt. % (preferably less than 0.2 wt. %, more preferably less than 0.15 wt. %, more preferably less than 0.1 wt. %) based on the extract.

In one preferred aspect the extract contain less than 1 wt. % of plant essential oils and/or oleoresins based on the extract. In one preferred aspect the extract contain less than 1 wt. % of plant essential oils and/or oleoresins based on the composition.

In one preferred aspect the extract contains essential oils in an amount of less than 1 wt. % based on the extract. In one preferred aspect the extract contains essential oils in an amount of less than 1 wt. % based on the composition.

In one preferred aspect the plant of the Labiatae family is selected from rosemary, sage, oregano, marjoram, mint, balm, savoury and thyme. In one preferred aspect the plant of the Labiatae family is selected from rosemary, sage, oregano, marjoram, mint, balm, and savoury. It will be understood that these name cover all species and varieties of plants known by these names.

In one preferred aspect the plant of the Labiatae family is selected from rosemary (*Rosmarinus officinalis* L.), sage (*Salvia officinalis* L) oregano (*Origanum vulgare* L.), marjoram (*Origanum marjorana* L.), mint (*Mentha* spp.), balm (*Melissa officinalis* L.), savoury (*Satureia hortensis*), thyme (*Thymus vulgaris* L.).

In one preferred aspect the plant of the Labiatae family is selected from rosemary (*Rosmarinus officinalis* L.), sage (*Salvia officinalis* L.), oregano (*Origanum vulgare* L.), marjoram (*Origanum marjorana* L.), mint (*Mentha* spp.), balm (*Melissa officinalis* L.), and savoury (*Satureia hortensis*).

In one preferred aspect the plant of the Labiatae family is selected from rosemary (*Rosmarinus officinalis* L.), sage (*Salvia officinalis* L.), marjoram (*Origanum marjorana* L.), mint (*Mentha* spp.), balm (*Melissa officinalis* L), and savoury (*Satureia hortensis*).

In one preferred aspect the plant of the Labiatae family is rosemary.

In a further preferred aspect the phenolic diterpenes, phenolic triterpenes and rosmarinic acid are obtained by chemical synthesis.

Thus in highly preferred aspects the present invention provides
- a composition comprising (a) an antimicrobial material and (b) a compound selected from carnosic acid, carnosol, methylcarnosic acid, betulinic acid, oleanolic acid, ursolic acid and rosmarinic acid (preferably carnosic acid and carnosol).
- a process for preventing and/or inhibiting the growth of, and/or killing a micro-organism in a material, the process comprising the step of contacting the material with (a) a bacteriocin; and (b) a compound selected from carnosic acid, carnosol, methylcarnosic acid, betulinic acid, oleanolic acid, ursolic acid and rosmarinic acid (preferably carnosic acid and carnosol).
- use of (a) an antimicrobial material and (b) a compound selected from carnosic acid, carnosol, methylcarnosic acid, betulinic acid, oleanolic acid, ursolic acid and rosmarinic acid (preferably carnosic acid and carnosol), for preventing and/or inhibiting the growth of, and/or killing a micro-organism in a material.

Microorganism

As discussed herein the present invention may prevent and/or inhibit the growth of, and/or kill a micro-organism in a material. This may be slowing or arresting a micro-organism, such a bacteria, or by killing the micro-organism present on contact with the present composition.

In one aspect the antimicrobial material and/or the extract are present in an amount to provide a microbicidal or microbiostatic effect.

In one aspect the bacteriocin and the extract are present in an amount to provide a microbicidal or microbiostatic effect.

In one aspect the bacteriocin and the extract are present in an amount to provide a microbicidal or microbiostatic synergistic effect.

In one aspect the bacteriocin and the extract are present in an amount to provide a microbicidal synergistic effect.

In a highly preferred aspect the microbicidal or microbiostatic effect is a bactericidal or bacteriostatic effect.

It is advantageous for the bactericidal or bacteriostatic effect to be in respect of Gram-positive bacteria and Gram-negative bacteria. Preferably the bactericidal or bacteriostatic effect is in respect of Gram-positive bacteria.

In a preferred aspect the bactericidal or bacteriostatic effect is in respect of an organism selected from Gram-positive bacteria associated with food spoilage or foodborne disease including *Bacillus* species, *Bacillus subtilis*, *Bacillus cereus*, *Listeria* species, *Listeria monocytogenes*, lactic acid bacteria, lactic acid spoilage bacteria, *Lactobacillus* species, *Staphylococcus aureus*, *Clostridium* species, *C. sporogenes*, *C. tyrobutyricum*.

In a preferred aspect the bactericidal or bacteriostatic effect of the invention in combination with a chelating agent is in respect of an organism selected from other microorganisms associated with food spoilage or foodborne disease, including yeasts, moulds and Gram-negative bacteria including *Escherichia coli*, *Salmonella* species, and *Pseudomonas* species.

In a preferred aspect the bactericidal or bacteriostatic effect is in respect of an organism selected from *Bacillus cereus* 204, *B. cereus* Campden, *B. cereus* NCTC2599, *B. subtilis* Campden, *Clostridium sporogenes* strain Campden, *Clostridium sporogenes* strain 1.221, *Clostridium sporo-* genes NCIMB1793, *Listeria monocytogenes* 272, *L. monocytogenes* NCTC12426, *L. monocytogenes* S23, *Lactobacillus sake* 272, *Escherichia coli* S15, *E. coli* CRA109, *Salmonella Typhimurium* S29, *Pseudomonas fluorescens* 3756, In a preferred aspect the bactericidal or bacteriostatic effect is in respect of *Listeria monocytogenes*.

Foodstuff

The composition, process and use of the present invention may prevent and/or inhibit the growth of, and/or kill a micro-organism in any material. However, in view of the problems associated with spoilage and contamination of foodstuffs and in view of the particular effectiveness of the present invention in foodstuffs, preferably the composition is a foodstuff or may be added to a foodstuff. It will be appreciated by one skilled in the art that when the present composition is a foodstuff the essential components of (a) an antimicrobial material and (b) a extract obtained from or obtainable from a plant of the Labiatae family are already present in the foodstuff. They may have been provided by one or more means. For example they may have been added in the form of a composition containing the bacteriocin and the extract. The two components (the bacteriocin and the afore mentioned extract) may have been added to the foodstuff sequentially. In one further aspect one or more of the components may have be formed in situ in the foodstuff. For example the bacteriocin may be formed in situ in the foodstuff by fermentation of the dairy starter culture bacterium *Lactococcus lactis* subsp. *lactis*.

In one aspect the composition of the present invention is a protectant composition suitable for addition to a foodstuff.

Many foodstuffs may be protected by the present invention. Typical foodstuffs are raw meat, cooked meat, raw poultry products, cooked poultry products, raw seafood products, cooked seafood products, ready to eat meals, pasta sauces, pasteurised soups, mayonnaise, salad dressings, oil-in-water emulsions, margarines, low fat spreads, water-in-oil emulsions, dairy products, cheese spreads, processed cheese, dairy desserts, flavoured milks, cream, fermented milk products, cheese, butter, condensed milk products, ice cream mixes, soya products, pasteurised liquid egg, bakery products, confectionery products, fruit products, and foods with fat-based or water-containing fillings.

Additional Components

The composition of the present invention or the composition for use in the present invention may contain one or more additional components. However, in some aspects the protectant composition of the present invention (suitable for addition to a foodstuff) contains no additional components or contains no additional components that materially affect the properties of the composition. In these aspects the present invention provides a composition consisting essentially of (a) a bacteriocin and (b) an extract obtained from or obtainable from a plant of the Labiatae family, wherein (a) and (b) are different a composition consisting of (a) a bacteriocin and (b) an extract obtained from or obtainable from a plant of the Labiatae family, wherein (a) and (b) are different a composition consisting essentially of (a) a bacteriocin and (b) an extract obtained from or obtainable from a plant of the Labiatae family, wherein (a) and (b) are different, wherein when the antimicrobial material consists of nisin, the composition comprises carvacrol in an amount of less than 0.075 wt. % based on the composition and carvone in an amount of less than 15 wt. % based on the composition.

a composition consisting of (a) a bacteriocin and (b) an extract obtained from or obtainable from a plant of the Labiatae family, wherein (a) and (b) are different, wherein when the antimicrobial material consists of nisin, the composition comprises carvacrol in an amount of less than 0.075 wt. % based on the composition and carvone in an amount of less than 15 wt. % based on the composition.

In one preferred aspect the composition further comprises an emulsifier. Preferably the emulsifier is selected from polyoxy-ethylene sorbitan esters (E432-E436) otherwise known as polysorbates (e.g. Tween 80, Tween 20), monoglycerides, diglycerides, acetic acid esters of mono-diglycerides, tartaric acid esters of mono-diglycerides and citric acid esters of mono-diglycerides.

In one preferred aspect the composition further comprises a chelator. Preferably the chelator is selected from EDTA, citric acid, monophosphates, diphosphates, triphosphates and polyphosphates.

Further suitable chelator are taught in U.S. Pat. No. 5,573,801 and include carboxylic acids, polycarboxylic acids, amino acids and phosphates. In particular, the following compounds and their salts may be useful:

Acetic acid, Adenine, Adipic acid, ADP, Alanine, B-Alanine, Albumin, Arginine, Ascorbic acid, Asparagine, Aspartic acid, ATP, Benzoic acid, n-Butyric acid, Casein, Citraconic acid, Citric acid, Cysteine, Dehydracetic acid, Desferriferrichrysin, Desferri-ferrichrome, Desferri-ferrioxamin E, 3,4-Dihydroxybenzoic acid, Diethylenetriaminepentaacetic acid (DTPA), Dimethylglyoxime, O,O-Dimethylpurpurogallin, EDTA, Formic acid, Fumaric acid, Globulin, Gluconic acid, Glutamic acid, Glutaric acid, Glycine, Glycolic acid, Glycylglycine, Glycylsarcosine, Guanosine, Histamine, Histidine, 3-Hydroxyflavone, Inosine, Inosine triphosphate, Iron-free ferrichrome, Isovaleric acid, Itaconic acid, Kojic acid, Lactic acid, Leucine, Lysine, Maleic acid, Malic acid, Methionine, Methylsalicylate, Nitrilotriacetic acid (NTA), Omithine, Orthophosphate, Oxalic acid, Oxystearin, B-Phenylalanine, Phosphoric acid, Phytate, Pimelic acid, Pivalic acid, Polyphosphate, Proline, Propionic acid, Purine, Pyrophosphate, Pyruvic acid, Riboflavin, Salicylaldehyde, Salicyclic acid, Sarcosine, Serine, Sorbitol, Succinic acid, Tartaric acid, Tetrametaphosphate, Thiosulfate, Threonine, Trimetaphosphate, Triphosphate, Tryptophan, Uridine diphosphate, Uridine triphosphate, n-Valeric acid, Valine, and Xanthosine Many of the above sequestering agents are useful in food processing in their salt forms, which are commonly alkali metal or alkaline earth salts such as sodium, potassium or calcium or quaternary ammonium salts. Sequestering compounds with multiple valencies may be beneficially utilised to adjust pH or selectively introduce or abstract metal ions e.g. in a food system coating. Additional information chelators is disclosed in T. E. Furia (Ed.), CRC Handbook of Food Additives, 2nd Ed., pp. 271-294 (1972, Chemical Rubber Co.), and M. S. Peterson and A. M. Johnson (Eds.), Encyclopaedia of Food Science, pp. 694-699 (1978, AVI Publishing Company, Inc.) which articles are both hereby incorporated by reference.

The terms "chelator" is defined as organic or inorganic compounds capable of forming co-ordination complexes with metals. Also, as the term "chelator" is used herein, it includes molecular encapsulating compounds such as cyclodextrin. The chelator may be inorganic or organic, but preferably is organic.

Preferred chelator are non-toxic to mammals and include aminopolycarboxylic acids and their salts such as ethylenediaminetetraacetic acid (EDTA) or its salts (particularly its di- and tri-sodium salts), and hydrocarboxylic acids and their salts such as citric acid. However, non-citric acid and non-citrate hydrocarboxylic acid chelators are also believed useful in the present invention such as acetic acid, formic acid, lactic acid, tartaric acid and their salts.

As noted above, the term "chelator" is defined and used herein as a synonym for sequestering agent and is also defined as including molecular encapsulating compounds such as cyclodextrin. Cyclodextrins are cyclic carbohydrate molecules having six, seven, or eight glucose monomers arranged in a donut shaped ring, which are denoted alpha, beta or gamma cyclodextrin, respectively. As used herein, cyclodextrin refers to both unmodified and modified cyclodextrin monomers and polymers. Cyclodextrin molecular encapsulators are commercially available from American Maize-Products of Hammond, Ind. Cyclodextrin are further described in Chapter 11 entitled, "Industrial Applications of Cyclodextrin", by J. Szejtli, page 331-390 of Inclusion Compounds, Vol. III (Academic Press, 1984) which chapter is hereby incorporated by reference.

Preferably the chelator enhances the antimicrobial activity and/or antimicrobial spectrum of the bacteriocin. More preferably the chelator enhances the antimicrobial activity and/or antimicrobial spectrum of the bacteriocin in respect of Gram-negative bacteria and other micro-organisms.

In one preferred aspect the composition further comprises a lytic enzyme. Preferably the lytic enzyme is a lysozyme.

Process

As discussed herein in one aspect the present invention provides process for preventing and/or inhibiting the growth of, and/or killing a micro-organism in a material, the process comprising the step of contacting the material with (a) an antimicrobial material; and (b) an extract obtained from or obtainable from a plant of the Labiatae family, wherein (a) and (b) are different; wherein the composition contains phenolic diterpenes in an amount of greater than 1.0 wt. %, based on the composition, and wherein when the antimicrobial material consists of nisin, the composition comprises carvacrol in an amount of less than 0.075 wt. % based on the composition and carvone in an amount of less than 15 wt. % based on the composition.

In one aspect the bacteriocin and the extract are added to the material together.

In one aspect the bacteriocin and the extract are added to the material sequentially.

Thus the present invention provides in one aspect a preservative/protectant composition which may be added to a range of materials such as food systems and in another aspect a combination of two separate products which may added sequentially to materials such as food products.

In one aspect the extract is added to the material.

In one aspect the bacteriocin is added to the material.

In one aspect the extract is formed in situ in the material.

In one aspect the bacteriocin is formed in situ in the material. Preferably when the bacteriocin is nisin, the bacteriocin may be formed in situ in the foodstuff by fermentation of the dairy starter culture bacterium *Lactococcus lactis* subsp. *lactis*.

Highly Preferred Aspects

As discussed herein in one aspect the present invention provides a process for preventing and/or inhibiting the growth of, and/or killing a micro-organism in a material, the process comprising the step of contacting the material with (a) an antimicrobial material; and (b) an extract obtained from or obtainable from a plant of the Labiatae family, wherein (a) and (b) are different; wherein when the antimicrobial material consists of nisin, the composition comprises carvacrol in an amount of less than 0.075 wt. % based on the composition and can/one in an amount of less than 15 wt. % based on the composition.

In one aspect the present invention provides use of (a) an antimicrobial material; and b) an extract obtained from or obtainable from a plant of the Labiatae family, for preventing and/or inhibiting the growth of, and/or killing a micro-organism in a material; wherein (a) and (b) are different; and wherein when the antimicrobial material consists of nisin, the composition comprises carvacrol in an amount of less than 0.075 wt. % based on the composition and carvone in an amount of less than 15 wt. % based on the composition.

Some highly preferred aspects of the present invention are set out below

- a composition comprising (a) a bacteriocin, wherein the bacteriocin is nisin; and (b) an extract obtained from a plant of the Labiatae family, wherein the composition contains phenolic diterpenes in an amount of greater than 1.0 wt. %, based on the composition, and wherein the composition comprises carvacrol in an amount of less than 0.075 wt. % based on the composition and carvone in an amount of less than 15 wt. % based on the composition.
- for preventing and/or inhibiting the growth of, and/or killing a micro-organism in a material, the process comprising the step of contacting the material with (a) a bacteriocin; wherein the bacteriocin is nisin; and (b) an extract obtained from or obtainable from a plant of the Labiatae family, wherein the composition contains phenolic diterpenes in an amount of greater than 1.0 wt. %, based on the composition, and wherein the composition comprises carvacrol in an amount of less than 0.075 wt. % based on the composition and carvone in an amount of less than 15 wt. % based on the composition.
- use of (a) a bacteriocin, wherein the bacteriocin is nisin; and (b) an extract obtained from or obtainable from a plant of the Labiatae family, for preventing and/or inhibiting the growth of, and/or killing a micro-organism in a material, wherein the composition contains phenolic diterpenes in an amount of greater than 1.0 wt. %, based on the composition, and the composition comprises carvacrol in an amount of less than 0.075 wt. % based on the composition and carvone in an amount of less than 15 wt. % based on the composition
- a composition comprising (a) a bacteriocin, and (b) an extract obtained from a plant of the Labiatae family selected from rosemary, sage, thyme, mint, balm, savoury and oregano, wherein (a) and (b) are different
- a process for preventing and/or inhibiting the growth of, and/or killing a micro-organism in a material, the process comprising the step of contacting the material with (a) a bacteriocin; and (b) an extract obtained from or obtainable from a plant of the Labiatae family selected from rosemary, sage, thyme, mint, balm, savoury and oregano, wherein (a) and (b) are different
- use of (a) a bacteriocin, and (b) an extract obtained from or obtainable from a plant of the Labiatae family selected from rosemary, sage, thyme, mint, balm, savoury and oregano, for preventing and/or inhibiting the growth of, and/or killing a micro-organism in a material, wherein (a) and (b) are different a composition comprising (a) a bacteriocin, and (b) a compound selected from carnosic acid, carnosol, methylcarnosic acid, betulinic acid, oleanolic acid, ursolic acid and rosmarinic acid.

a process for preventing and/or inhibiting the growth of, and/or killing a micro-organism in a material, the process comprising the step of contacting the material with (a) a bacteriocin, and (b) a compound selected from carnosic acid, carnosol, methylcarnosic acid, betulinic acid, oleanolic acid, ursolic acid and rosmarinic acid.

use of (a) a bacteriocin, and (b) a compound selected from carnosic acid, carnosol, methylcarnosic acid, betulinic acid, oleanolic acid, ursolic acid and rosmarinic acid, for preventing and/or inhibiting the growth of, and/or killing a micro-organism in a material.

a composition comprising (a) a bacteriocin, and (b) carnosic acid.

a process for preventing and/or inhibiting the growth of, and/or killing a micro-organism in a material, the process comprising the step of contacting the material with (a) a bacteriocin, and (b) carnosic acid.

use of (a) a bacteriocin, and (b) carnosic acid, for preventing and/or inhibiting the growth of, and/or killing a micro-organism in a material.

a composition comprising (a) a bacteriocin, wherein the bacteriocin is nisin; and (b) an extract obtained from or obtainable from a plant of the Labiatae family selected from rosemary, thyme, mint, balm, savoury, sage and oregano, wherein the composition contains phenolic diterpenes in an amount of greater than 1.0 wt. %, based on the composition, and wherein the composition comprises carvacrol in an amount of less than 0.075 wt. % based on the composition and carvone in an amount of less than 15 wt. % based on the composition.

a process for preventing and/or inhibiting the growth of, and/or killing a micro-organism in a material, the process comprising the step of contacting the material with (a) a bacteriocin; wherein the bacteriocin is nisin; and (b) a selectively extracted extract obtained from or obtainable from a plant of the Labiatae family selected from rosemary, sage, thyme, mint, balm, savoury and oregano, wherein the composition contains phenolic diterpenes in an amount of greater than 1.0 wt. %, based on the composition, and wherein the composition comprises carvacrol in an amount of less than 0.075 wt. % based on the composition and carvone in an amount of less than 15 wt. % based on the composition.

use of (a) a bacteriocin, wherein the bacteriocin is nisin; and (b) a selectively extracted extract obtained from or obtainable from a plant of the Labiatae family selected from rosemary, sage, thyme, mint, balm, savoury and oregano, for preventing and/or inhibiting the growth of, and/or killing a micro-organism in a material, wherein the composition contains phenolic diterpenes in an amount of greater than 1.0 wt. %, based on the composition, and wherein the composition comprises carvacrol in an amount of less than 0.075 wt. % based on the composition and carvone in an amount of less than 15 wt. % based on the composition.

a composition comprising (a) a bacteriocin, wherein the bacteriocin is nisin; and (b) a compound selected from carnosic acid, carnosol, methylcarnosic acid, betulinic acid, oloanolic acid, ursolic acid and rosmarinic acid, wherein the composition contains phenolic diterpenes in an amount of greater than 1.0 wt. %, based on the composition, and wherein the composition comprises carvacrol in an amount of less than 0.075 wt. % based on the composition and carvone in an amount of less than 15 wt. % based on the composition.

a process for preventing and/or inhibiting the growth of, and/or killing a micro-organism in a material, the process comprising the step of contacting the material with (a) a bacteriocin, wherein the bacteriocin is nisin; and (b) a compound selected from carnosic acid, carnosol, methylcarnosic acid, betulinic acid, oloanolic acid, ursolic acid and rosmarinic acid, wherein the composition contains phenolic diterpenes in an amount of greater than 1.0 wt. %, based on the composition, and wherein the composition comprises carvacrol in an amount of less than 0.075 wt. % based on the composition and carvone in an amount of less than 15 wt. % based on the composition.

use of (a) a bacteriocin, wherein the bacteriocin is nisin; and (b) a compound selected from carnosic acid, carnosol, methylcarnosic acid, betulinic acid, oloanolic acid, ursolic acid and rosmarinic acid, for preventing and/or inhibiting the growth of, and/or killing a micro-organism in a material, wherein the composition contains phenolic diterpenes in an amount of greater than 1.0 wt. %, based on the composition, and wherein the composition comprises carvacrol in an amount of less than 0.075 wt. % based on the composition and carvone in an amount of less than 15 wt. % based on the composition.

a composition comprising (a) a bacteriocin, wherein the bacteriocin is nisin; and (b) carnosic acid.

a process for preventing and/or inhibiting the growth of, and/or killing a micro-organism in a material, the process comprising the step of contacting the material with (a) a bacteriocin, wherein the bacteriocin is nisin; and (b) carnosic acid.

use of (a) a bacteriocin, wherein the bacteriocin is nisin; and (b) carnosic acid, for preventing and/or inhibiting the growth of, and/or killing a micro-organism in a material.

a composition comprising (a) a bacteriocin, wherein the bacteriocin is nisin; and (b) an extract obtained from a plant of the Labiatae family selected from rosemary, sage, thyme, mint, balm, savoury and oregano, wherein the bacteriocin and the extract are present in an amount to provide a bactericidal or bacteriostatic synergistic effect, wherein the composition contains phenolic diterpenes in an amount of greater than 1.0 wt. %, based on the composition, and wherein the composition comprises carvacrol in an amount of less than 0.075 wt. % based on the composition and carvone in an amount of less than 15 wt. % based on the composition.

a process for preventing and/or inhibiting the growth of, and/or killing a micro-organism in a material, the process comprising the step of contacting the material with (a) a bacteriocin; wherein the bacteriocin is nisin; and (b) an extract obtained from or obtainable from a plant of the Labiatae family selected from rosemary, sage, thyme, mint, balm, savoury and oregano, wherein the bacteriocin and the extract are present in an amount to provide a bactericidal or bacteriostatic synergistic effect wherein the composition contains phenolic diterpenes in an amount of greater than 1.0 wt. %, based on the composition, and wherein the composition comprises carvacrol in an amount of less than 0.075 wt. % based on the composition and carvone in an amount of less than 15 wt. % based on the composition.

use of (a) a bacteriocin, wherein the bacteriocin is nisin; and (b) an extract obtained from or obtainable from a plant of the Labiatae family selected from rosemary, sage, thyme, mint, balm, savoury and oregano, for preventing and/or inhibiting the growth of, and/or killing a micro-organism in a material, wherein the bacteriocin and the extract are present in an amount to provide a bactericidal or bacteriostatic synergistic effect, wherein the composition contains phenolic diterpenes in an amount of greater than 1.0 wt. %, based on the composition, and wherein the composition comprises carvacrol in an amount of less than 0.075 wt. % based on the composition and carvone in an amount of less than 15 wt. % based on the composition.

a composition comprising (a) a bacteriocin, wherein the bacteriocin is nisin; and (b) a compound selected from carnosic acid, carnosol, methylcarnosic acid, betulinic acid, oleanolic acid, ursolic acid and rosmarinic acid, wherein the bacteriocin and the compound are present in an amount to provide a bactericidal or bacteriostatic synergistic effect wherein the composition contains phenolic diterpenes in an amount of greater than 1.0 wt. %, based on the composition, and wherein the composition comprises carvacrol in an amount of less than 0.075 wt. % based on the composition and carvone in an amount of less than 15 wt. % based on the composition.

a process for preventing and/or inhibiting the growth of, and/or killing a micro-organism in a material, the process comprising the step of contacting the material with (a) a bacteriocin, wherein the bacteriocin is nisin; and (b) a compound selected from carnosic acid, carnosol, methylcarnosic acid, betulinic acid, oleanolic acid, ursolic acid and rosmarinic acid, wherein the bacteriocin and the compound are present in an amount to provide a bactericidal or bacteriostatic synergistic effect wherein the composition contains phenolic diterpenes in an amount of greater than 1.0 wt. %, based on the composition, and wherein the composition comprises carvacrol in an amount of less than 0.075 wt. % based on the composition and carvone in an amount of less than 15 wt. % based on the composition.

use of (a) a bacteriocin, wherein the bacteriocin is nisin; and (b) a compound selected from carnosic acid, carnosol, methylcarnosic acid, betulinic acid, oleanolic acid, ursolic acid and rosmarinic acid, for preventing and/or inhibiting the growth of, and/or killing a micro-organism in a material, wherein the bacteriocin and the compound are present in an amount to provide a bactericidal or bacteriostatic synergistic effect wherein the composition contains phenolic diterpenes in an amount of greater than 1.0 wt. %, based on the composition, and wherein the composition comprises carvacrol in an amount of less than 0.075 wt. % based on the composition and carvone in an amount of less than 15 wt. % based on the composition.

a composition comprising (a) a bacteriocin, wherein the bacteriocin is nisin; and (b) a compound selected from carnosic acid, wherein the bacteriocin and the compound are present in an amount to provide a bactericidal or bacteriostatic synergistic effect a process for preventing and/or inhibiting the growth of, and/or killing a micro-organism in a material, the process comprising the step of contacting the material with (a) a bacteriocin, wherein the bacteriocin is nisin; and (b) a compound selected from carnosic acid, wherein the bacteriocin and the compound are present in an amount to provide a bactericidal or bacteriostatic synergistic effect use of (a) a bacteriocin, wherein the bacteriocin is nisin; and (b) a compound selected from carnosic acid, for preventing and/or inhibiting the growth of, and/or killing a micro-organism in a material, wherein the bacteriocin and the compound are present in an amount to provide a bactericidal or bacteriostatic synergistic effect a composition comprising (a) a bacteriocin, wherein the bacteriocin is nisin; and (b) an extract obtained from a plant of the Labiatae family, wherein the composition contains phenolic diterpenes in an amount of greater than 1.0 wt. %, based on the composition, wherein the composition comprises carvacrol in an amount of less than 0.04 wt. % based on the composition and carvone in an amount of less than 0.04.% based on the composition.

a process for preventing and/or inhibiting the growth of, and/or killing a micro-organism in a material, the process comprising the step of contacting the material with (a) a bacteriocin; wherein the bacteriocin is nisin; and (b) an extract obtained from or obtainable from a plant of the Labiatae family, wherein the composition contains phenolic diterpenes in an amount of greater than 1.0 wt. %, based on the composition, wherein the composition comprises carvacrol in an amount of less than 0.04 wt. % based on the composition and carvone in an amount of less than 0.04.% based on the composition.

use of (a) a bacteriocin, wherein the bacteriocin is nisin; and (b) an extract obtained from or obtainable from a plant of the Labiatae family, for preventing and/or inhibiting the growth of, and/or killing a micro-organism in a material, wherein the composition contains phenolic diterpenes in an amount of greater than 1.0 wt. %, based on the composition, wherein the composition comprises carvacrol in an amount of less than 0.04 wt. % based on the composition and carvone in an amount of less than 0.04.% based on the composition.

Further broad aspects of the present invention are defined below:

a composition comprising (a) an antimicrobial material; and (b) an extract obtained from or obtainable from a plant of the Labiatae family, wherein (a) and (b) are different; wherein the composition contains phenolic diterpenes in an amount of greater than 1.0 wt. %, based on the composition.

a process for preventing and/or inhibiting the growth of, and/or killing a micro-organism in a material, the process comprising the step of contacting the material with (a) an antimicrobial material; and (b) an extract obtained from or obtainable from a plant of the Labiatae family, wherein (a) and (b) are different; wherein the composition contains phenolic diterpenes in an amount of greater than 1.0 wt. %.

use of (a) an antimicrobial material; and b) an extract obtained from or obtainable from a plant of the Labiatae family, for preventing and/or inhibiting the growth of, and/or killing a micro-organism in a material; wherein (a) and (b) are different; wherein the composition contains phenolic diterpenes in an amount of greater than 1.0 wt. %.

a kit for preparing a composition as defined herein, the kit comprising (a) an antimicrobial material; and (b) an extract obtained from or obtainable from a plant of the Labiatae family, wherein (a) and (b) are different; wherein the composition contains phenolic diterpenes in an amount of greater than 1.0 wt. %, based on the composition.

a composition comprising (a) an antimicrobial material; and (b) an extract obtained from or obtainable from a plant of the Labiatae family, wherein (a) and (b) are different; wherein when the antimicrobial material consists of nisin, the composition comprises carvacrol in an amount of less than 0.075 wt. % based on the composition and carvone in an amount of less than 15 wt. % based on the composition.

a process for preventing and/or inhibiting the growth of, and/or killing a micro-organism in a material, the process comprising the step of contacting the material with (a) an antimicrobial material; and (b) an extract obtained from or obtainable from a plant of the Labiatae family, wherein (a) and (b) are different; wherein when the antimicrobial material consists of nisin, the composition comprises carvacrol in an amount of less than 0.075 wt. % based on the composition and carvone in an amount of less than 15 wt. % based on the composition.

use of (a) an antimicrobial material; and b) an extract obtained from or obtainable from a plant of the Labiatae family, for preventing and/or inhibiting the growth of, and/or killing a micro-organism in a material; wherein (a) and (b) are different; wherein when the antimicrobial material consists of nisin, the composition comprises carvacrol in an amount of less than 0.075 wt. % based on the composition and carvone in an amount of less than 15 wt. % based on the composition.

a kit for preparing a composition as defined herein, the kit comprising (a) an antimicrobial material; and (b) an extract obtained from or obtainable from a plant of the Labiatae family, wherein (a) and (b) are different; wherein when the antimicrobial material consists of nisin, the composition comprises carvacrol in an amount of less than 0.075 wt. % based on the composition and carvone in an amount of less than 15 wt. % based on the composition, in separate packages or containers; optionally with instructions for admixture and/or contacting and/or use.

The present invention will now be described in further detail by way of example only with reference to the accompanying figures in which:—

FIG. 1 is a graph showing synergistic enhancement of nisin cidal activity against *Listeria monocytogenes* in chicken soup at 25° C. by a selectively extracted rosemary extract FIG. 2 is a graph showing synergistic enhancement of nisin control of *Listeria monocytogenes* growth in chilled chicken soup by a selectively extracted rosemary extract (GRE09)

FIG. 3 is a graph showing synergistic enhancement by a selectively extracted rosemary extract of nisin control of *B. cereus* spore outgrowth in chilled chicken soup. Minimal detection limit was 100 cfu/g. For the length of the testing period, the samples containing the combination of nisin and rosemary had *Bacillus* counts at or below 100 cfu/g.

Figure 1:
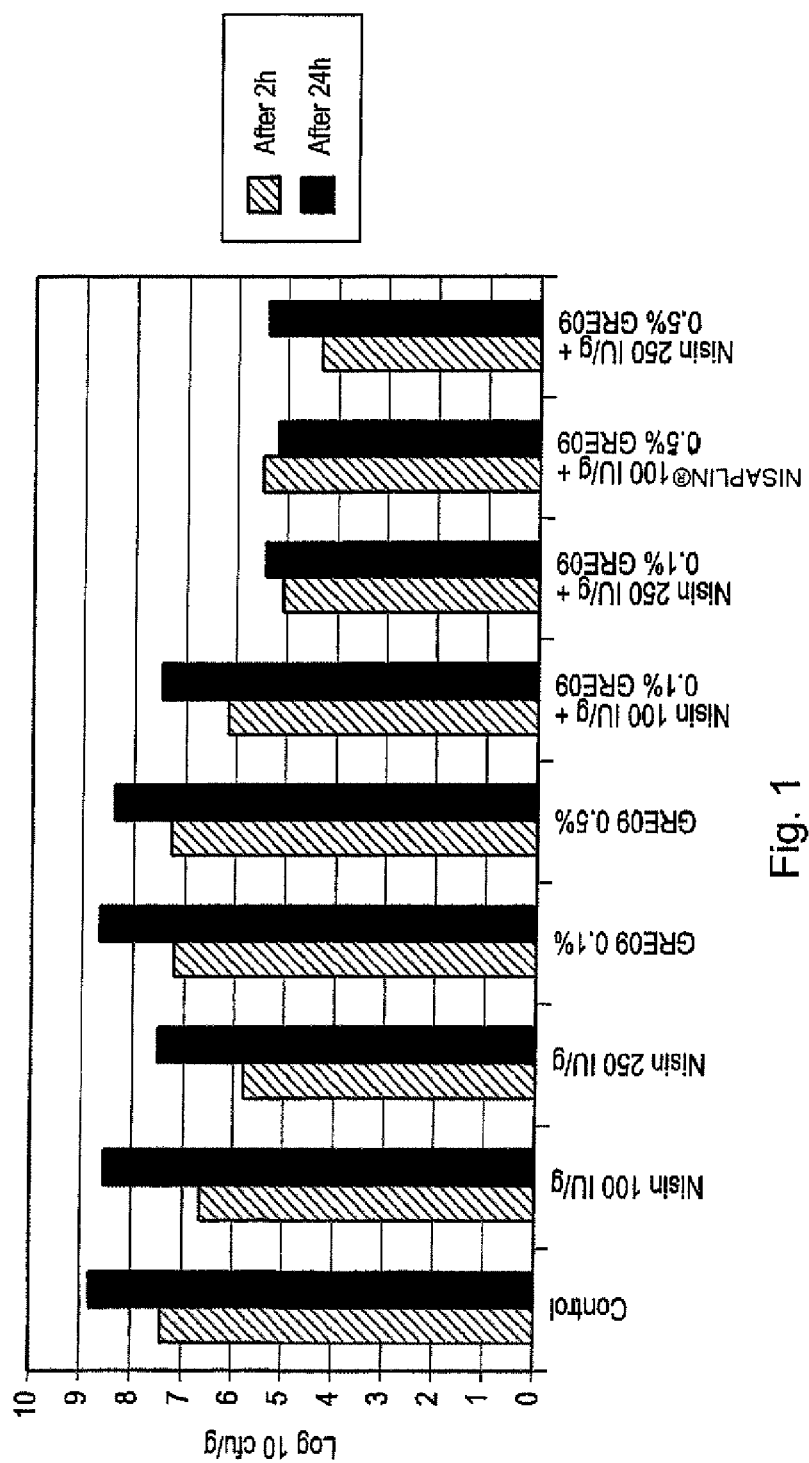

The present invention will now be described in further detail in the following examples.

EXAMPLES

Experimental Evidence of Benefit

In vitro studies described herein have shown synergy between nisin and extracts of *Rosmarinus officinalis* containing >3.5% phenolic diterpenes, increasing the efficacy of nisin significantly. This enhanced activity was also observed in food models, increasing nisin kill and growth control of Gram-positive bacteria. The experimental studies also demonstrated that the phenolic diterpenes camosic acid and camosol were implicated in this synergy. The results also indicated that rosmarinic acid may also enhance nisin activity, although this synergistic effect was not as strong as that observed with the phenolic diterpenes.

I) In Vitro Demonstration of Nisin and Deodorised Rosemary Extract Synergy

Materials:

GUARDIAN™ Rosemary Extract 09 (Danisco) (GRE09). This is a water dispersible deodorised rosemary extract containing 4% phenolic diterpenes and <1% essential oils, extracted from rosemary leaves, combined with the carriers polyoxyethylene sorbitan monooleate (Tween 80) and propylene glycol. A commercial extract of nisin at potency of 1×10$^6$ IU/g: NISAPLIN® Natural Antimicrobial (Danisco).

Test Strains:

*Bacillus cereus* 204, *B. cereus* Campden, *B. cereus* NCTC2599, *B. subtilis* Campden, *Listeria monocytogenes* 272, *L. monocytogenes* NCTC12426, *L. monocytogenes* S23, *Lactobacillus sake* 272, *Escherichia coli* S15, *E. coli* CRA109, *Salmonella Typhimurium* S29, *Pseudomonas fluorescens* 3756.

Method of Microbial Growth Curve Analysis.

A 100,000 ppm GRE09 solution was prepared in water and filter sterilised (0.2 μm). Further dilutions were prepared in sterile deionised water at 1,250-20,000 ppm. Brain Heart Infusion broth (Oxoid) was prepared and GRE09 stock solutions were added to give the following test solutions of GRE09; 125, 250, 500, 750, 1000, 1250, 1500, 2000 ppm.

A 10,000 IU/ml nisin solution was prepared, filter sterilised and a range of stock solutions then prepared. A range of nisin concentrations was then prepared in Brain Heart Infusion broth. A fully automated microbial growth analyser was used to determine microbial growth curves (Microbiology Reader Bioscreen C analyser linked to a PC with installed software BioLink v 5.30; Labsystem Oy, Finland). Tests were prepared in honeycomb 2 (HC 2) microtitre/cuvette plates with a capacity of 100 wells per plate. The wells were loaded with 270 μl of the prepared media and inoculated at a level of $10^3$ CFU (colony forming units)/ml with 30 μl of microbial suspension. Incubation time and temperature was as appropriate for the test organism. This test allowed suitable test levels for the compounds to be determined. The rosemary extract and nisin were then tested in combination, using the same procedure. Nisin solutions were prepared at 50-1000 IU/ml in broth as above. GRE09 solutions were prepared at 250, 500 and 1000 ppm as above. Combinations of all these test levels were prepared and tested in the Bioscreen as before.

Results:

The minimum inhibitory concentration of nisin alone, rosemary extract GRE09 alone and the two in combination in the Bioscreen after 48 h at 30° C. is shown in Table 1. The minimal inhibition was taken as the lowest concentration that caused total inhibition of the bacteria after 48 h at 30° C. Synergy was observed between nisin and the rosemary extract GRE09 against all Gram-positive bacteria but no significant effect was observed against Gram-negative bacteria. This can be determined from the table by comparing the column of data showing MIC levels of nisin alone, GRE09 alone and the two combined. The latter column gave levels much lower than the other two for Gram-positive bacteria (*Bacillus, Listeria*) but not for Gram-negative bacteria (*E. coli, Salmonella*).

TABLE 1

Synergy tests of nisin and the rosemary extract GRE09

| Test organism | MIC in broth after 48 h at 30° C. (total inhibition) | | | Other test levels of the combination causing total inhibition |
|---|---|---|---|---|
| | Nisin (IU/ml) | GRE09 (ppm) | MIC of nisin (IU/ml) + GRE09 (ppm) | Nisin (IU/ml) + GRE09 (ppm) |
| *B. cereus* 204 | 500 | >1000 | 50 + 250 | 50 + 500 |
| | | | | 50 + 1000 |
| | | | | 100 + 250 |
| | | | | 100 + 500 |
| | | | | 100 + 1000 |
| | | | | 200 + 250 |
| | | | | 200 + 500 |
| | | | | 200 + 1000 |
| *B. cereus* NCTC2599 | 500 | >1000 | 50 + 250 | 50 + 500 |
| | | | | 50 + 1000 |
| | | | | 100 + 250 |
| | | | | 100 + 500 |
| | | | | 100 + 1000 |
| | | | | 200 + 250 |
| | | | | 200 + 500 |
| | | | | 200 + 1000 |
| *B. subtilis* Campden | 100 | >1000 | 50 + 250 | 50 + 500 |
| | | | | 50 + 1000 |
| | | | | 100 + 250 |
| | | | | 100 + 600 |
| | | | | 100 + 1000 |
| | | | | 200 + 250 |
| | | | | 200 + 500 |
| | | | | 200 + 1000 |
| *L. monocytogenes* S23 | >500 | >1000 | 50 + 250 | 50 + 500 |
| | | | | 50 + 1000 |
| | | | | 100 + 250 |
| | | | | 100 + 500 |
| | | | | 100 + 1000 |
| | | | | 200 + 250 |
| | | | | 200 + 500 |
| | | | | 200 + 1000 |
| *L. monocytogenes* 272 | >500 | >1000 | 50 + 250 | 50 + 500 |
| | | | | 50 + 1000 |
| | | | | 100 + 250 |
| | | | | 100 + 500 |
| | | | | 100 + 1000 |
| | | | | 200 + 250 |
| | | | | 200 + 500 |
| | | | | 200 + 1000 |
| *L. monocytogenes* 12426 | >500 | >1000 | 50 + 250 | 50 + 500 |
| | | | | 50 + 1000 |
| | | | | 100 + 250 |
| | | | | 100 + 500 |
| | | | | 100 + 1000 |
| | | | | 200 + 250 |
| | | | | 200 + 500 |
| | | | | 200 + 1000 |

TABLE 1-continued

Synergy tests of nisin and the rosemary extract GRE09

| Test organism | MIC in broth after 48 h at 30° C. (total inhibition) | | | Other test levels of the combination causing total inhibition |
|---|---|---|---|---|
| | Nisin (IU/ml) | GRE09 (ppm) | MIC of nisin (IU/ml) + GRE09 (ppm) | Nisin (IU/ml) + GRE09 (ppm) |
| E. coli S15 | >500 | >1000 | >1000 + >1000 | — |
| E. coli CRA109 | >500 | >1000 | >1000 + >1000 | — |
| S. Typhimurium S29 | >500 | >1000 | >1000 + >1000 | — |
| Ps. fluorescens 3756 | >500 | >1000 | >1000 + >1000 | — |

Figure 2:
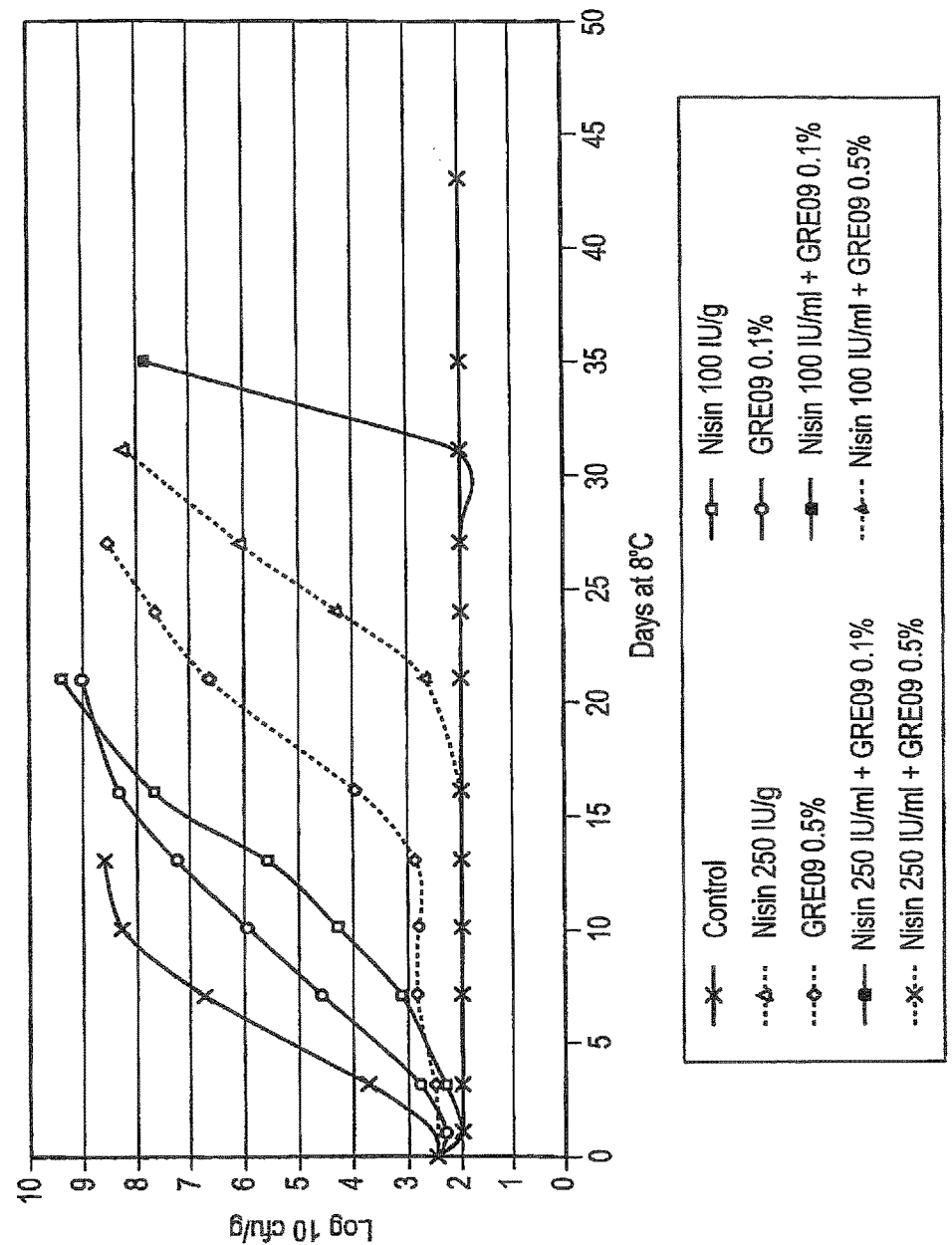

II) Demonstration of Nisin and Rosemary Extract GRE09 Synergy in Food
A) Synergy Against *Listeria monocytogenes*
Test Compounds:
GRE09 at 0.1%, 0.5%, NISAPLIN® (Danisco).
Test Strains:
a cocktail was prepared of *L. monocytogenes* strains NCTC12426, NCTC5105, NCC FSM60 and CRA3930. The *Listeria* strains were grown at 30° C. on Brain heart infusion agar overnight then inoculated into broth at 30° C. overnight. A volume of each broth was mixed together to give a cocktail of strains with a cell concentration of approximately $10^9$ CFU/ml.
Media:
A chilled pasteurised chicken soup was used as a food model because it was a good mix of different food components including vegetables, dairy products and poultry meat. It was comprised of a chicken stock with the addition of chicken, cream, vegetables, flour and seasonings. The pH was 6.12. After addition of nisin and rosemary extract GRE09, the soup was pasteurised at a core temperature of 80° C. for 2 minutes. The *Listeria* cocktail was diluted to $10^4$ CFU/ml and inoculated into soup tests to give a final cell count of approximately $10^2$ CFU/g (growth inhibitory tests) and $10^7$ CFU/ml (cidal tests). The latter test was incubated at 25° C. for 2 h and then tested by viable count enumeration to estimate the extent of cidal activity. The growth test was incubated at 8° C. with regular sampling to estimate bacteriostatic activity.
Results.
The rosemary extract GRE09 alone at 0.5% showed no listericidal activity. Nisin at 250 IU/g caused a 1 log drop in *Listeria* numbers after 2 h, but only a slight delay in growth after 24 h (FIG. 1). In comparison the combination of the two test products at these levels caused a 2-3 log drop in *Listeria* numbers after 2 h. After 24 h the cells still had not recovered to their initial inoculum level. This was a particularly harsh test for any preservative system, since the test medium was a rich food model, the incubation temperature was at ambient and the bacterial numbers high. Therefore any enhanced nisin activity was a good indication of synergy.
Incubation for the bacteriostatic test was for 43 days: results of this are shown in FIG. 2 and Table 2. The nisin/rosemary synergy was again clearly demonstrated in the food model against the *Listeria* cocktail. For example, *Listeria* growth reached $10^6$ CFU/ml after 13 days in the presence of 100 IU/ml nisin; after 10 days in the presence of 0.1% GRE09 but only after a much longer period, 34 days, in the presence of the combination of these two ingredients. Similarly, *Listeria* growth reached $10^6$ CFU/ml after 13 days in the presence of 100 IU/ml nisin; after 20 days in the presence of 0.5% GRE09. The combination of the two components resulted in no growth being observed by then end of the test period.

TABLE 2

Summary of growth inhibition of *Listeria* in chilled chicken soup (Trial lasted 43 days)

| Test conditions | Days until growth reached $10^6$ CFU/ml |
|---|---|
| Control | 6 |
| Nisin at 100 IU/ml | 13 |
| Nisin at 250 IU/ml | 27 |
| Rosemary extract GRE09 at 0.1% | 10 |
| Rosemary extract GRE09 at 0.5% | 20 |
| Nisin (100 IU/ml) + GRE09 at 0.1% | 34 |
| NISAPLIN (100 IU/ml) + GRE09 at 0.5% | >43 |
| NISAPLIN (250 IU/ml) + GRE09 at 0.1% | >43 |
| NISAPLIN (250 IU/ml) + GRE09 at 0.5% | >43 |

During the test period (a) NISAPLIN (100 IU/ml) + GRE09 at 0.5%, (b) NISAPLIN (250 IU/ml) + GRE09 at 0.1%, and (c) NISAPLIN (250 IU/ml) + GRE09 at 0.5% did not give any total aerobic viable counts above 100 cfu/g.

Figure 3:
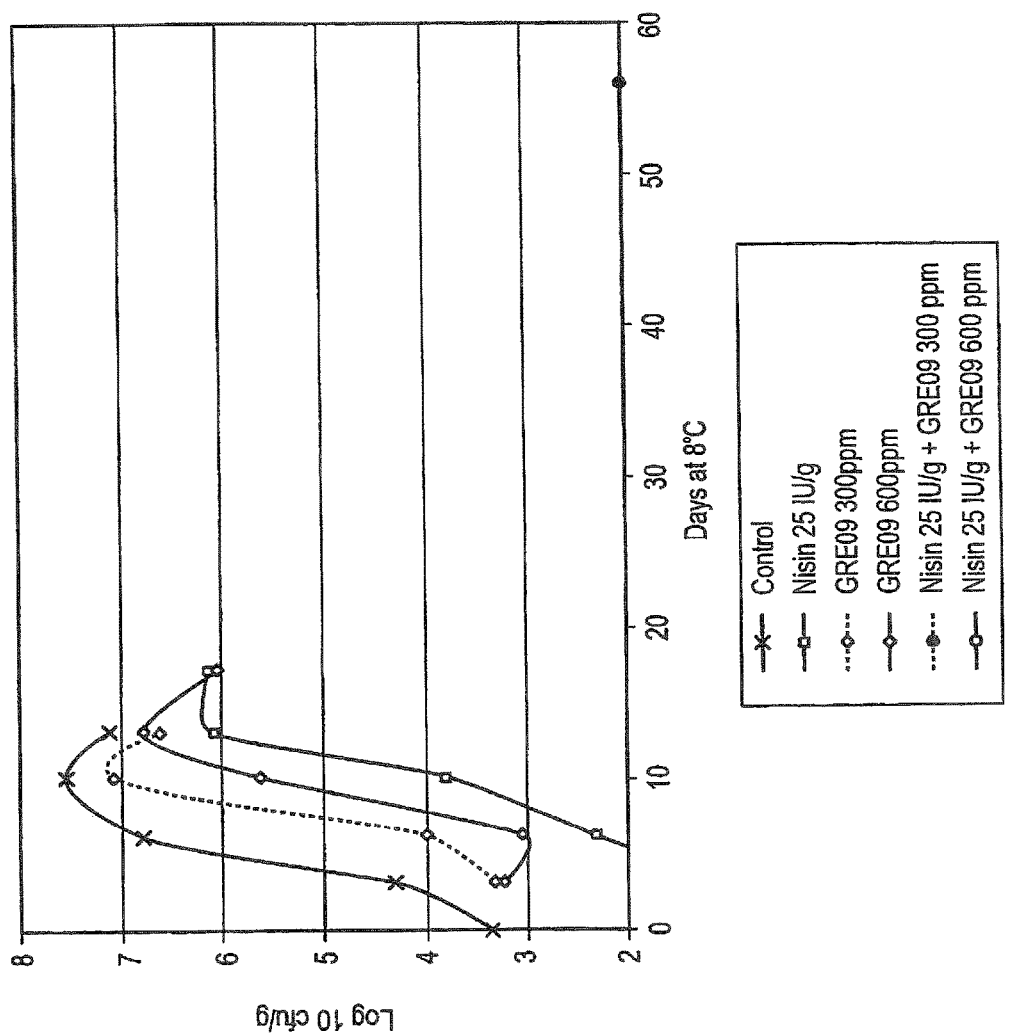
Figure 4:
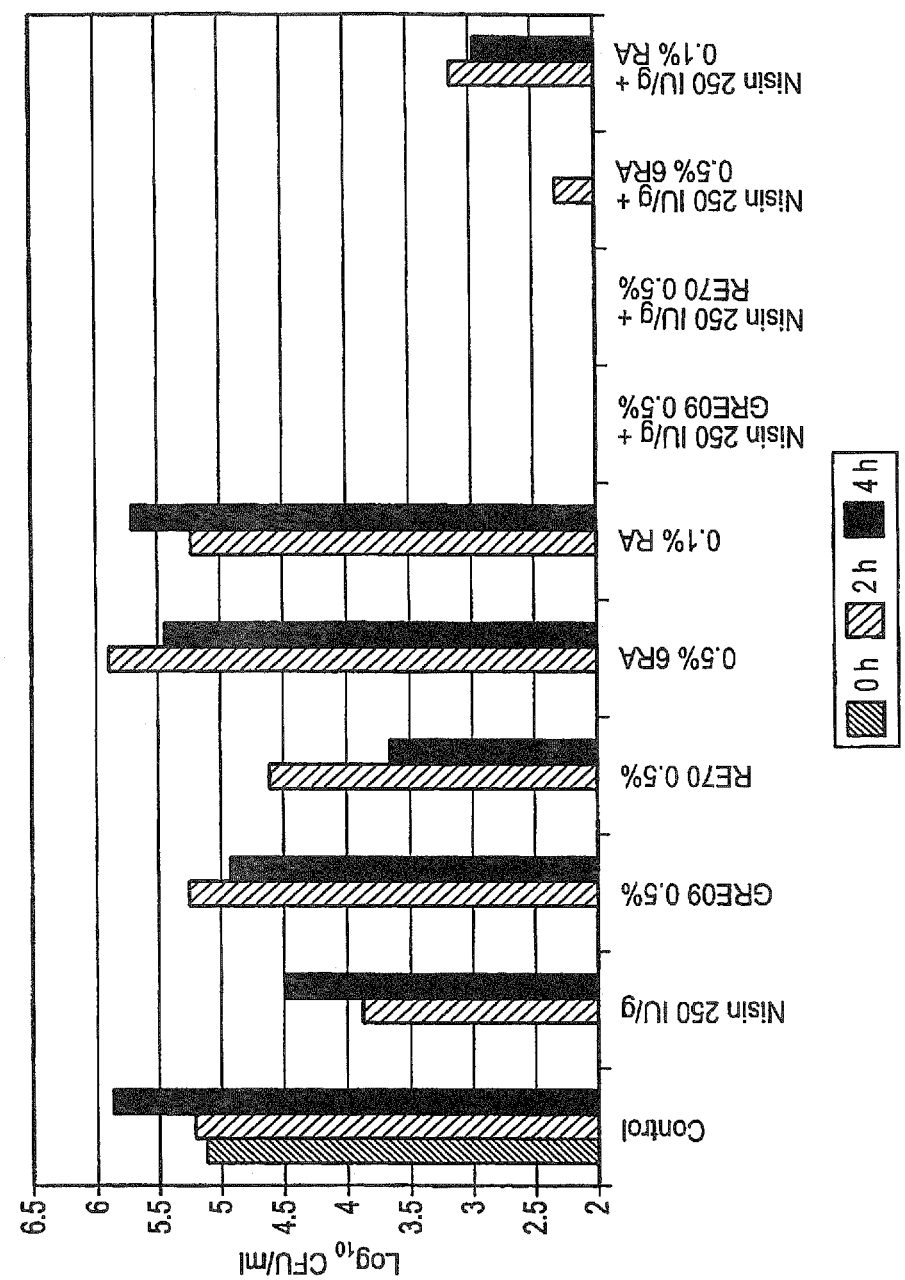
FIG. 4 is a graph showing combined effect of nisin, selectively extracted rosemary extracts and rosemary extract components against *L. monocytogenes* in chicken soup at 20° C. (Minimum detection limit 100 cfu/g)
Figure 5:
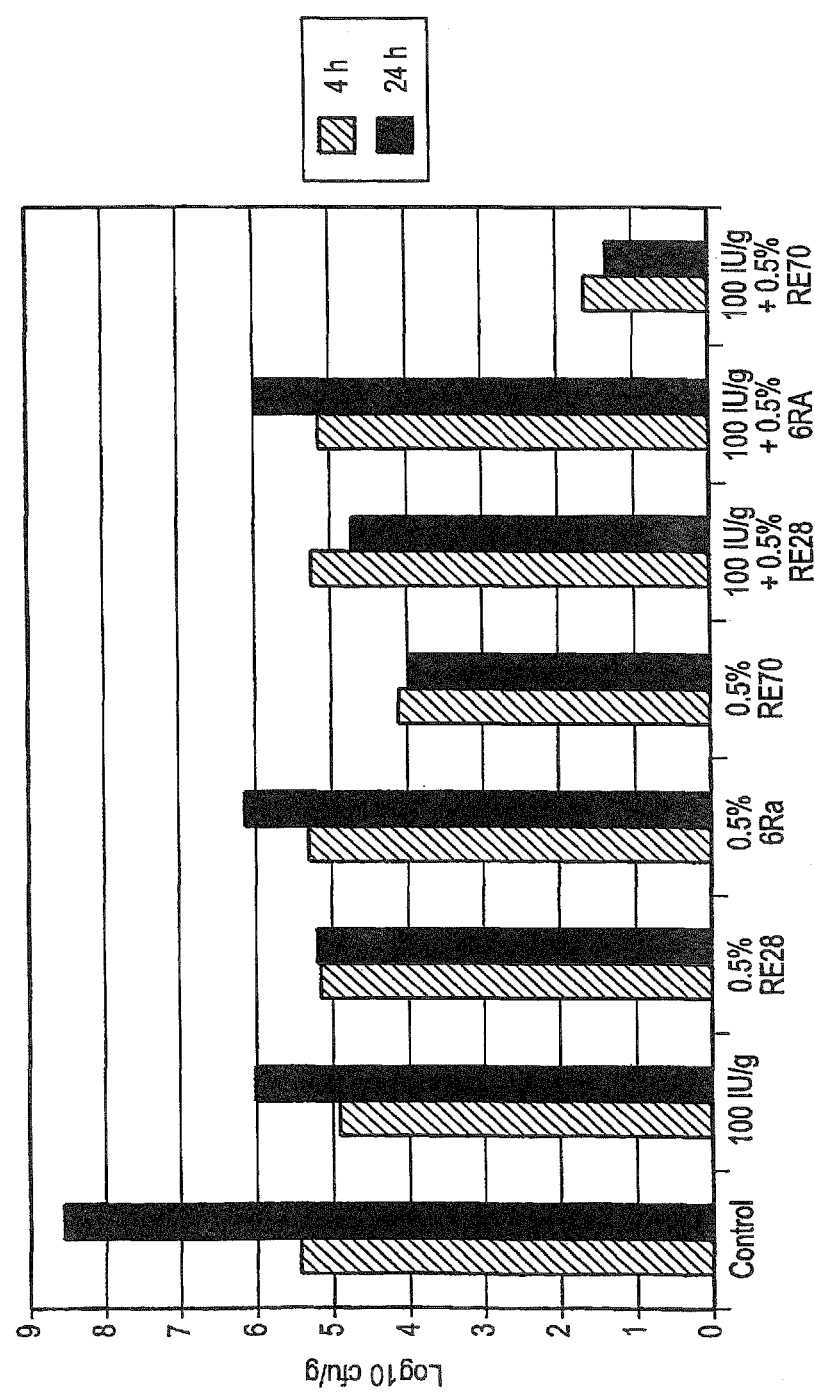
FIG. 5 is a graph showing synergistic enhancement of nisin activity by selectively extracted extracts of rosemary or rosmarinic acid against *Listeria monocytogenes* in a chicken soup at ambient temperature.

B) Synergy Against *Bacillus cereus*
Test Strains:
a cocktail of *Bacillus* spores was prepared as an inoculum, using *Bacillus cereus* strain 204, *Bacillus cereus* strain 199, *B. cereus* strain Campden, and *B. cereus* strain ABC 4/9.
Additions of the test compounds were made to chicken soup, prepared as above. The soup was pasteurised at 70° C. for 2 minutes, cooled and inoculated with approximately $10^3$ CFU/g of a cocktail of *Bacillus cereus* spores. Incubation was for 56 days. Results are shown in FIG. 3 and summarised in Table 3. Bacteriostatic synergy between the nisin and rosemary extract GRE09 was evident. For example, spoilage (i.e. $10^6$ CFU/ml) resulted after 13 days in the presence of 25 IU/ml nisin, and after 10 days in the presence of 300 ppm GRE09. In the presence of both these ingredients, no spoilage had occurred by the end of the trial (56 days).

TABLE 3

Summary of results of chilled chicken soup trial inoculated with *Bacillus cereus* spores (Trial lasted 70 days).

| Test conditions | Days until growth reached $10^6$ CFU/ml |
|---|---|
| Control | 6 |
| Nisin at 25 IU/ml | 13 |
| Rosemary extract GRE09 at 300 ppm | 10 |
| Rosemary extract GRE09 at 600 ppm | 13 |
| Nisin (25 IU/ml) + GRE09 at 300 ppm | >70 |

TABLE 3-continued

Summary of results of chilled chicken soup trial inoculated with
*Bacillus cereus* spores (Trial lasted 70 days).

| Test conditions | Days until growth reached $10^6$ CFU/ml |
|---|---|
| NISAPLIN (25 IU/ml) + GRE09 at 600 ppm | >70 |

C) Synergy Against *Clostridium sporogenes*

Test Strains:

a cocktail of *Clostridium* spores was prepared as an inoculum, using *Clostridium sporogenes* strain Campden, *Clostridium sporogenes* 1.221, and *Clostridium sporogenes* NCIMB1793.

Additions of the test compounds were made to chicken soup, prepared as above. The soup was pasteurised at 70° C. for 2 minutes and transferred to sterile test tubes. These were inoculated with a cocktail of heat-shocked *Clostridium sporogenes* spores, at a level of $2.2\times10^2$ CFU/g, then anaerobic conditions were created by plugging the tubes with agar. The samples were incubated at 37° C. and checked daily for gas production (observed by blowing of the gas plug and by the distinctive clostridial odour). Results for a 27 day incubation period, demonstrating synergy, are shown in Table 4. For example, synergy was clearly seen by the combined effect of 50 IU/ml nisin and 300 ppm GRE09, which prevented growth for 27 days (the length of the trial), whereas the individual ingredients both prevented clostridial growth for 2 days (the same as the control).

TABLE 4

Summary of results of chicken soup trial inoculated with *Clostridium sporogenes* spores incubated at 37° C. (Trial lasted 27 days).

| Test conditions | Days until growth observed (gas production) |
|---|---|
| Control | 2 |
| Nisin at 25 IU/ml | 2 |
| Nisin at 50 IU/ml | 2 |
| Nisin at 100 IU/ml | 7 |
| Rosemary extract GRE 09 at 300 ppm | 2 |
| Rosemary extract GRE 09 at 600 ppm | 2 |
| Nisin (25 IU/ml) + GRE 09 at 300 ppm | 3 |
| Nisin (50 IU/ml) + GRE 09 at 300 ppm | >27 |
| Nisin (100 IU/ml) + GRE 09 at 300 ppm | >27 |
| NISAPLIN (25 IU/ml) + GRE 09 at 600 ppm | 10 |
| NISAPLIN (100 IU/ml) + GRE 09 at 600 ppm | >27 |

III) Demonstration of In Vitro Synergy with Different Deodorised, Selectively Extracted Rosemary Extracts and Rosmarinic Acid Growth curves of *Listeria monocytogenes* and *B. cereus* strains in laboratory media were analysed as described above using the Bioscreen C analyser. Minimal inhibitory concentrations (MIC) were determined for the test compounds used singly or in combination after 24 h at 30° C. Results are shown in Table 5. The test compounds comprised nisin (as Nisaplin®; Danisco), GRE09 (Danisco), pure rosmarinic acid (RA; Sigma) and a range of deodorised rosemary extracts. These had been prepared by selected extraction with either organic solvents or $CO_2$ to obtain extracts containing 28% phenolic diterpenes (28RE; Danisco) and a rosemary extract containing 6% rosmarinic acid (6RA; Danisco). Enhanced nisin activity was evident with a combination of nisin combined with pure rosmarinic acid (RA; this may have partly been due to low pH levels), a combination of nisin with a rosemary extract containing 6% rosmarinic acid (6RA) and a combination of nisin with a deodorised rosemary extract containing 28% phenolic diterpenes and <1% essential oils (28RE). The known nisin synergy with Tween 80 was also observed. The other carrier propylene glycol did not enhance nisin activity. The synergies can be observed, as before, by comparing the MIC levels for nisin alone, the other test compound, and the two together (see Table 5).

TABLE 5

MIC after growth at 30° C. in laboratory medium

| Test organism | MIC in Bioscreen after 24 h at 30° C. | |
|---|---|---|
| | Individual components | Combination with nisin |
| *L. monocytogenes* strain S23 | Nisin at 1000 IU/ml | — |
| | 0.1% GRE09 | 0.05% GRE09 + 50 IU/ml nisin |
| | 1% RA | 0.25% RA + 250 IU/ml nisin |
| | | 0.5% RA + 100 IU/ml nisin |
| | | 0.75% RA + 50 IU/ml nisin |
| | 1% 6RA | <0.1% 6RA + 250 IU/ml nisin |
| | | 0.5% 6RA + 50 IU/ml nisin |
| *L. monocytogenes* strain 272 | 500 IU/ml nisin | — |
| | 0.25% GRE09 | <0.05% GRE09 + 50 IU/ml nisin |
| | 1% of RE28 | <0.05% RE28 + 50 IU/ml nisin |
| | >2% Tween 80 | 0.5% Tween 80 + 250 IU/ml nisin |
| *L. monocytogenes* strain NCTC12426 | 250 IU/ml nisin | — |
| | 0.25% GRE09 | <0.05% GR 09 + 50 IU/ml nisin |
| | 1% of RE28 | <0.05% RE28 + 50 IU/ml nisin |
| | >2% Tween 80 | 0.5% Tween 80 + 100 IU/ml nisin |
| *B. cereus* Campden spores | 500 IU/ml nisin | — |
| | 0.1% GRE09 | 0.05% GRE09 + 50 IU/ml |
| | 1% RA | 0.5% RA + 250 IU/ml nisin |
| | | 0.75% RA + 100 IU/ml nisin |
| | | 0.75% RA + 50 IU/ml nisin |
| | 1% 6RA | 0.25% 6RA + 100 IU/ml nisin |
| | | 0.5% 6RA + 50 IU/ml nisin |

IV) Demonstration of Synergy for Nisin Activity with Different Deodorised Rosemary Extract Components in Food Test Strains:

*Listeria monocytogenes* strains 272, CRA3930 and NCTC12426

The chicken soup model was used as before. The following samples were tested: GRE09, deodorised rosemary extracts containing 28% or 70% phenolic diterpenes (RE28 and RE70; Danisco), a water soluble rosemary extract containing 6% rosmarinic acid (6RA; Danisco) and pure rosmarinic acid (RA; Sigma). Additions to the soup were made as appropriate. The soup was pasteurised (70° C./2 minutes), the pH recorded and the soup was then inoculated with a cocktail of *Listeria* cells prepared as described before. The tests were incubated at 20° C. and viable count enumeration performed after 0, 2, 4 and 24 h at 20° C. Initial *Listeria* levels were $1.3\times10^5$ CFU/ml. The test was repeated at two nisin levels and over different time periods. The pH of the soup without addition was pH 6.06-6.20. Addition of rosmarinic acid at 0.1% resulted in a slight pH drop to pH 5.75. Addition of 6% RA resulted in a soup pH of pH 5.75-5.78. Addition of 0.5% RE28 resulted in a soup pH of pH 5.98. Addition of 0.5% RE70 resulted in a soup pH of pH 6.10. Addition of 0.5% GRE09 resulted in a soup pH of pH 6.02-6.09.

Results, shown in FIGS. 4 and 5, indicate that all the deodorised extracts tested and rosmarinic acid contributed to synergy with nisin in achieving kill of *Listeria* cells. This could not be attributed to the drop in pH caused by some of the additions. The additional synergy with Tween 80 was observed in GRE09. The results indicate that the antioxidant compounds carnosol and carnosic acid, present at 28 and 70% in two of the extracts tested, synergistically enhanced the cidal and growth inhibitory activity of nisin against *Listeria monocytogenes*. A nisin synergy with rosmarinic acid was evident but not as strong.

V) Demonstration of Synergistic Enhancement of Nisin's Growth Inhibitory Activity in Different Food Systems Using a Blend of Nisin with a Phenolic Diterpene-Containing Rosemary Extract A) Pasteurised Chicken Soup Tests
Method:

Different additions of nisin (as Nisaplin®, Danisco), a Rosemary extract containing 28% phenolic diterpenes (RE28), and a blend of nisin with the Rosemary extract at levels of 50 IU/mg and 4.2% phenolic diterpenes were added to commercial chicken soup that contained no other preservatives. After addition of the compounds the soup (pH 5.8) was pasteurised at a core temperature of 70° C. for 2 minutes. The soup was cooled to ambient temperature and either inoculated with a cocktail of stationary phase cells of *Listeria monocytogenes* strains or spores of *Bacillus cereus*. The strain cocktails comprised: *L. monocytogenes* strains NCIMB12426, strain 358, strain 272, strain CRA3930. The *B. cereus* cocktail comprised strains 204, 199, ABC4/9 and 3.046. Initial inoculum levels were approximately $10^2$-$10^3$ CFU/g. *Bacillus* tests were incubated at 15° C., *Listeria* tests were incubated at 8° C. Microbiological analysis was conducted at regular intervals (Milk Plate count Agar, Oxford *Listeria* Selective agar).

Figure 6:
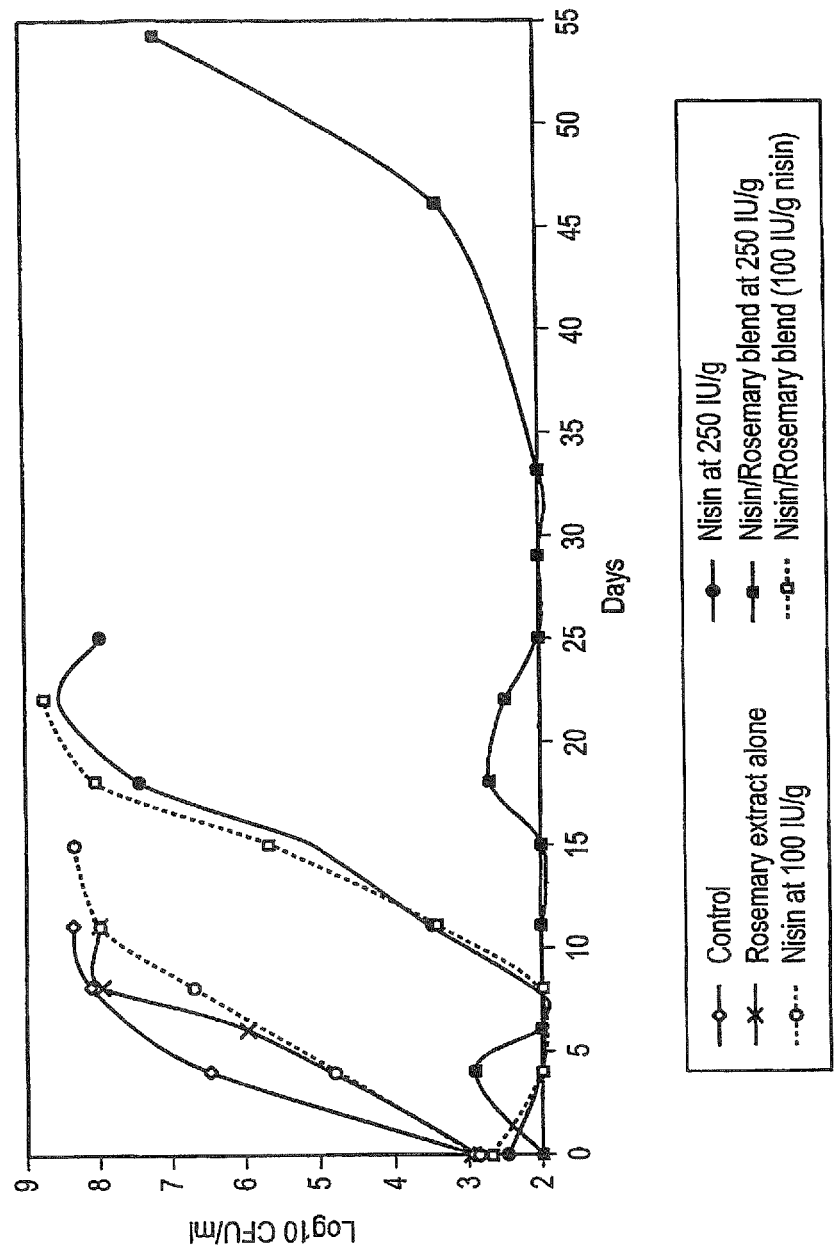
FIG. 6 is a graph showing a demonstration of synergy between nisin and phenolic diterpene-containing rosemary extract. Inhibition of *L. monocytogenes* at 8° C.
Figure 7:
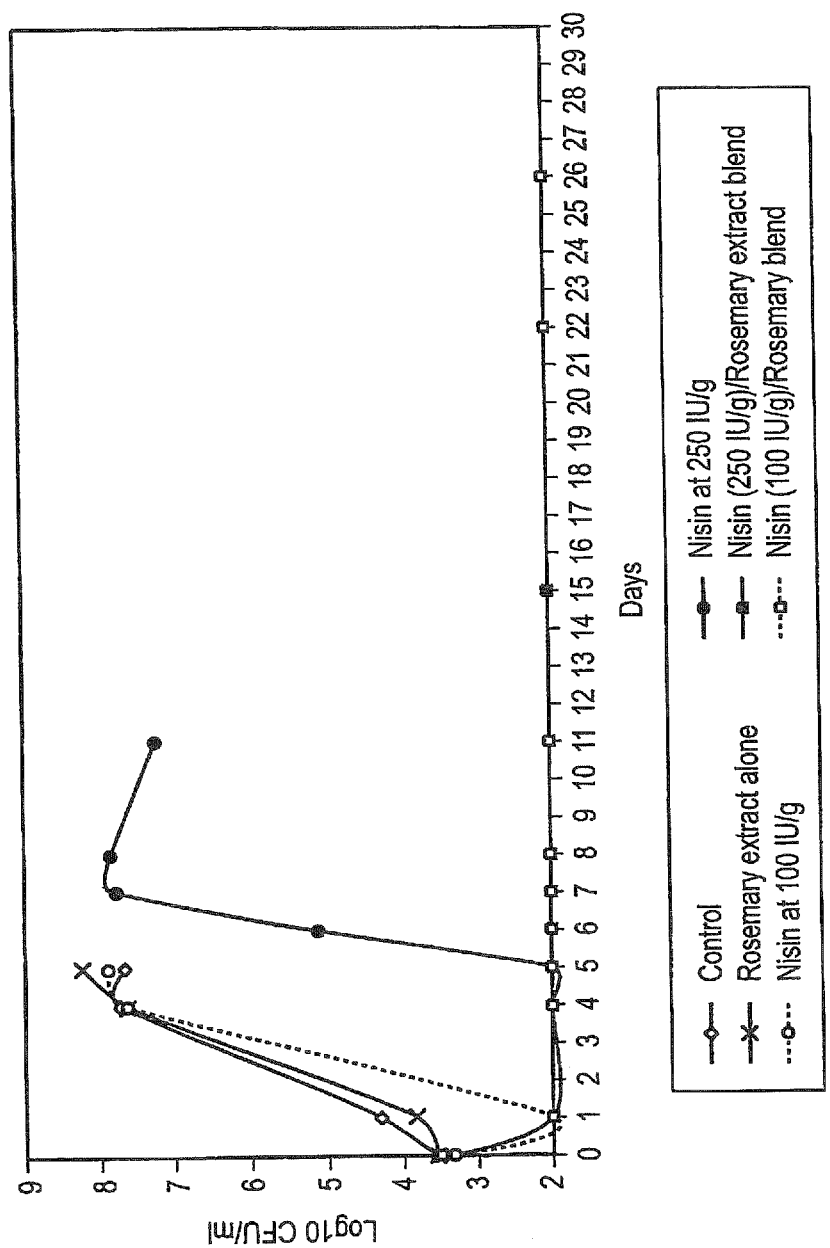
FIG. 7 is a graph showing a demonstration of synergy between nisin and phenolic diterpene-containing rosemary extract. Inhibition of *B. cereus* at 15° C.

Results:

The results, shown as the time taken for bacterial numbers to reach $10^6$ CFU/g, are summarised in Table 5. The full data are shown in FIGS. 6 and 7. The results show that the Rosemary extract alone had no activity against *Bacillus*, and only slight activity against *Listeria*. The Rosemary extract significantly enhanced the growth inhibitory activity of nisin.

TABLE 5

Summary of results demonstrating nisin/phenolic diterpene synergy against *Listeria* and *Bacillus* in a pasteurised chicken soup

| Test | Nisin content | Phenolic diterpene content | Days until growth reached $10^6$ CFU/g | |
| --- | --- | --- | --- | --- |
| | | | *L. monocytogenes* at 8° C. | *B. cereus* at 15° C. |
| Control | 0 | | 3 | 2 |
| RE28 at 75 ppm | 0 IU/g | 21 ppm | 5 | 2 |
| NISAPLIN at 100 mg/kg | 100 IU/g | 0 ppm | 6 | 3 |
| NISAPLIN at 250 mg/kg | 250 IU/g | 0 ppm | 16 | 6 |
| Nisin/Rosemary blend A | 100 IU/g | 8.4 pm | 15 | >26 |
| Nisin/Rosemary blend B | 250 IU/g | 21 ppm | 52 | >26 |

B) Pasteurised Meat Pasta Sauce Tests
Method:

The sauce was prepared from lean minced beef (50%), tomatoes and juice (48.9%), starch (0.5%), salt (0.4%) and sucrose (0.2%). The beef was fried for 5 minutes until brown, then the dry ingredients mixed in followed by the tomatoes with juice. The sauce was simmered for 10 minutes and allowed to cool before blending to a smooth consistency. Final pH was 5.13. Additions were made of nisin, rosemary extract and blends. The sauce was pasteurised to a core temperature of 80° C. for 2 minutes. A cocktail of *Listeria monocytogenes* strains (as above) were inoculated after pasteurisation and the tests incubated at 8° C.

Results:

The results, shown as the time taken for bacterial numbers to reach $10^6$ CFU/g, are summarised in Table 6. These show that the rosemary extract alone had no activity against *Bacillus*, and only slight activity against *Listeria*. The rosemary extract significantly enhanced the growth inhibitory activity of nisin.

TABLE 6

Summary of results demonstrating nisin/phenolic diterpene synergy against *Listeria* in a pasteurised meat sauce at 8° C.

| Test | Nisin | Phenolic diterpene | Days until $10^6$ CFU/g |
| --- | --- | --- | --- |
| Control | 0 | 0 | 4 |
| RE28 at 60 ppm | 0 IU/g | 16.8 ppm | 5 |
| NISAPLIN at 100 mg/kg | 100 IU/g | 0 ppm | 11 |
| Nisin/Rosemary blend A | 100 IU/g | 8.4 pm | >76 |

C) Carbonara Pasta Sauce Tests
Method:

A commercial chilled pasteurised sauce was used, containing cream, smoked bacon, cheese, mascarpone, butter, starch, onion, garlic puree. Protein 7 g, carbohydrate 6 g, fat 17 g. Additions of test compounds were made prior to the pasteurisation (core temperature of 70° C. for 10 minutes). Inoculations were made once the sauce had cooled. Samples were analysed regularly for microbial numbers.

Figure 8:
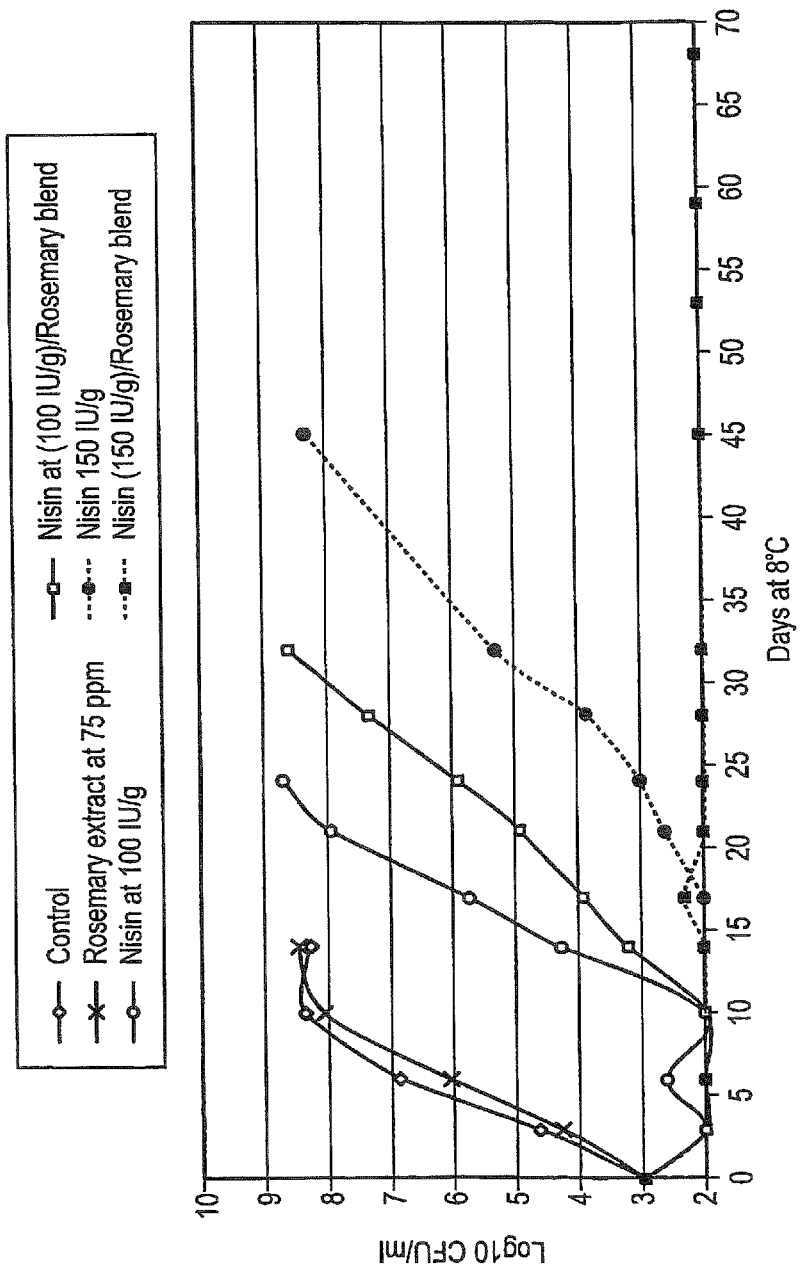
FIG. 8 is a graph showing enhanced nisin growth inhibitory activity by a phenolic diterpene-containing rosemary extract. Control of *L. monocytogenes* in carbonara sauce at 8° C.
Figure 9:
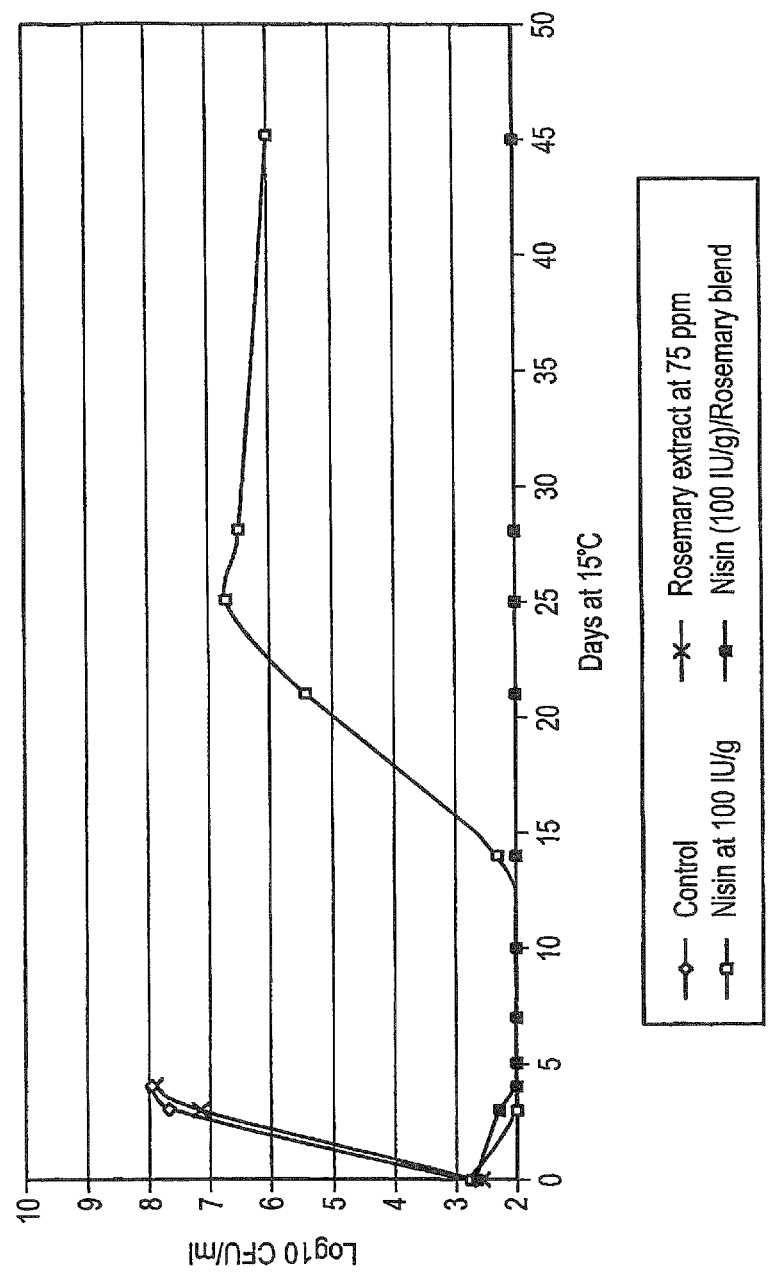
FIG. 9 is a graph showing enhanced nisin growth inhibitory activity by a phenolic diterpene-containing rosemary extract. Control of *B. cereus* spores in carbonara sauce at 15° C.

Results:

These are shown in FIGS. 8 and 9. As before, the phenolic diterpene-containing extract (8.4 ppm) synergistically enhanced the nisin growth inhibitory activity against *Listeria* cells and *Bacillus* spores. The rosemary extract alone showed no activity.

VI) Demonstration of Synergistic Enhancement of Nisin's Cidal Activity in a Food System Using a Blend of Nisin with Phenolic Diterpene-Containing Rosemary Extract Method:

The diluted chicken soup (pH 6.2) was prepared as above, and split into 2 batches with one batch being adjusted to pH 4.5 with HCl. Appropriate additions of nisin, rosemary extract and blends were made, then the soup was pasteurised. A cocktail of *Listeria* strains was inoculated to give an initial inoculum of $10^5$ CFU/g. Viable cells were enumerated by microbiological analysis at 0 and 2 h.

The test blends contained 1) 100 IU/g nisin+30 ppm rosemary extract (i.e. 8.4 phenolic diterpenes), and 2) 150 IU/g nisin+45 ppm rosemary extract (i.e. 12.6 phenolic diterpenes).

Figure 10:
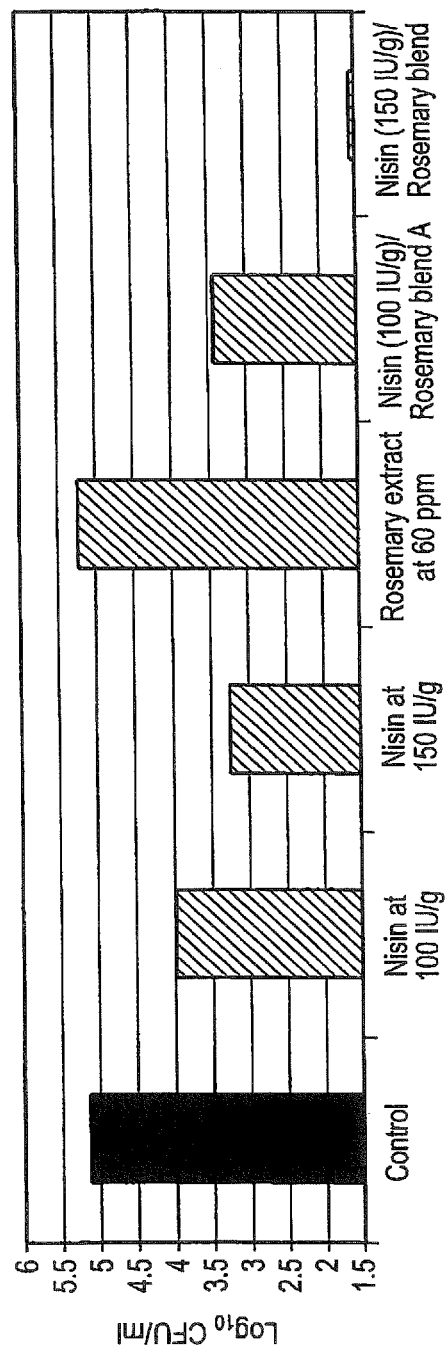
FIG. 10 is a graph showing enhanced cidal effect of a nisin and phenolic diterpene-containing rosemary extract against *L. monocytogenes* in chicken soup at 20° C. a) pH 4.5
Figure 11:
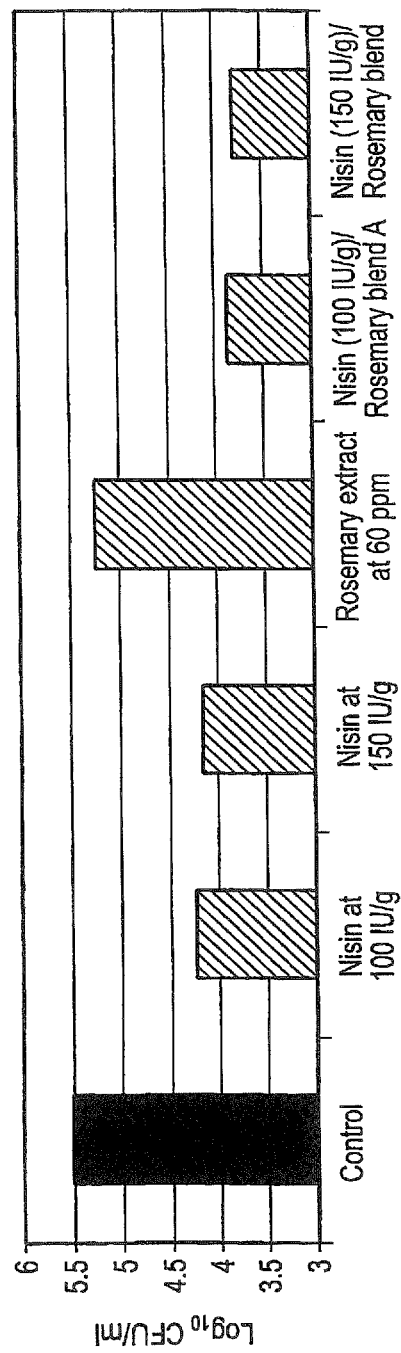
FIG. 11 is a graph showing enhanced cidal effect of a nisin and phenolic diterpene-containing rosemary extract against *L. monocytogenes* in chicken soup at 20° C. b) pH 6.7

Results:

The results demonstrated that the presence of the phenolic diterpene containing rosemary extract synergistically enhanced the cidal activity of nisin (FIGS. 10 and 11), particularly at more acidic conditions (FIG. 10). The rosemary extract alone had no significant cidal effect.

REFERENCES

Bacteriocin+Rosemary Combination
JP 07-03955 & JP 3042573 (Asam Kasei KK, Lion Corp)
JP 3040282 (Asam Kasei KK)
Nisin+Tween 80 Synergy
Jung, D.-S, Bodyfelt, F. W. and Daeschel, M. 1992. Influence of fat and emulsifiers on the efficacy of nisin in inhibiting *Listeria monocytogenes* in fluid milk. Journal of Dairy Science 75: 387-393
Synergy Between Essential Oils and Nisin
Pol, I. E., Krommer, J., and Smid, E. 2002. Bioenergetic consequences of nisin combined with carvacrol towards *Bacillus cereus*. Innovative Food Science and Emerging Technologies 3: 55-61.
Pol, I. E. and Smid, E. J. 1999. Combined action of nisin and carvacrol on *Bacillus cereus* and *Listeria monocytogenes*. Letters in Applied Microbiology 29: 166-170.
Pol, I. E. 2001. Improved applicability of nisin in novel combinations with other food preservation factors. Ph.D thesis Wageningen University, The Netherlands ISBN 90-5808-382-9
Periago, P. M., Palop, A., Fernandez, P. S. 2001. Combined effect of nisin, carvacrol and thymol on the viability of *Bacillus cereus* treated vegetative cells. Food Science and Technology International 7: 487-492.
Antimicrobial Activity of Rosemary
Aureli, P., Constantini, A., and Zolea, S. 1992. Antimicrobial activity of some plant essential oils against *Listeria monocytogenes*. Journal of Food Protection 55:344-348.
Azzouz, M. A. and Bullerman, L. B. 1982. Comparative antimycotic effects of selected herbs, spices, plant components and commercial antifungal agents. Journal of Food Protection 45: 1298-1301
Collins, M. A., and Charles, H. P. 1987. Antimicrobial activity of Carnosol and Ursolic acid: two anti-oxidant constituents of *Rosmarinus officinalis* L. Food Microbiology 4: 311-315
Deans, S. G. and Ritchie, G. 1987. Antibacterial activity of plant essential oils. International Journal of Food Microbiology 5: 165-180.
Del Campo, J., Amiot, M.-J., and Nguyen-The, C. 2000. Antimicrobial effect of Rosemary extracts. Journal of Food Protection. 63:1359-1368.
Del Campo, J., Amiot, M.-J., Lapierre, C., and Nguyen-The, C. 1998. Antimicrobial activity of phenolic extracts from rosemary. 2nd International Electronic Conference on Synthetic Organic Chemistry (ECS)C-2), http://www.m-dpi.org/ecsoc/, Sep. 1-30, 1998
Eiserle, R. J. 1971. Gemini rising—a natural flavouring and stabilisation system for food. Food Prod. Dev. 10: 70-71
Farag, R. S., Daw, Z. Y., Hewedi, F. M. and El-Baroty, G. S. A. 1989. Antimicrobial activity of some Egyptian spice essential oils. Journal of Food Protection 52: 665-667
Farbood, M. I., MacNeil, J. H. and Ostovar, K. 1976. Effect of Rosemary spice extractive on growth of micro-organisms in meat. Journal of Milk Food Technology. 39:675-679
MacNeil, J. H., Dimick, P. S., and Mast, M. G. 1973. Use of chemical compounds and a rosemary spice extractive in quality maintenance of deboned poultry meat. Journal of Food Science 38: 1080-1081
MacNeil, J. H., and Mast, M. G. 1973. Frankfurters without nitrates and nitrites. Food Prod. Dev. 7: 36-40
Pandit, V. A. and Shelef, L. A. 1994. Sensitivity of *Listeria monocytogenes* to rosemary. Food Microbiology 11: 57-63
Shelef, L. A. 1983. Antimicrobial effects of spices. Journal of Food Safety 6:29-44
Shelef, L. A., Naglik, O. A., and Bogen, D. W. 1980. Sensitivity of some common food-borne bacteria to the spices sage, rosemary and allspice. Journal of Food Science 45:1042-1044
Valero, M. and Salmeron, M. C. 2003. Antibacterial activity of 11 essential oils against *Bacillus cereus* in tyndallized carrot broth. International Journal of Food Microbiology 85: 73-81
Zaika, L. L. 1988. Spices and herbs: their antimicrobial activity and its determination. Journal of Food Safety 9:97-118
Antimicrobial Activity of Sage
Akgul, A. and Kivanc, M. 1989. Sensitivity of four food-borne moulds to essential oils from Turkish spices, herbs and citrus peel. J. Sci. Food Agric. 47: 129-132
Aureli, P., Constantini, A., and Zolea, S. 1992. Antimicrobial activity of some plant essential oils against *Listeria monocytogenes*. Journal of Food Protection 55:344-348
Azzouz, M. A. and Bullerman, L. B. 1982. Comparative antimycotic effects of selected herbs, spices, plant components and commercial antifungal agents. Journal of Food Protection 45: 1298-1301
Deans, S. G. and Ritchie, G. 1987. Antibacterial activity of plant essential oils. International Journal of Food Microbiology 5: 165-180
Farag, R. S., Daw, Z. Y., Hewedi, F. M. and El-Baroty, G. S. A. 1989. Antimicrobial activity of some Egyptian spice essential oils. Journal of Food Protection 52: 665-667
Haq, I. 1982. Bull. Islamic Med. 2: 496
Ikram, M. and Haq, I. 1980. Screening of medicinal plants for antimicrobial activity. Part I. Fitoterapia 51: 231-235.
Leslie, G. B. 1978. Medita B 10: 3
Moujir, L., Gutierrez-Navarro, A. M., Andres, L. S. Luis, J. G. 1993. Structure-antimicrobial activity relationships of abietane diterpenes from *Salvia* species. Phytochemistry 34: 1493-1495
Ross, S. A., El-Ketawi, N. E. and Megalla, S. E. 1980. Antimicrobial activity of some Egyptian aromatic plants. Fitoterapia 51: 201-205.
Shelef, L. A., Naglik, O. A., and Bogen, D. W. 1980. Sensitivity of some common food-borne bacteria to the spices sage, rosemary and allspice. Journal of Food Science 45:1042-1044
Phenolic Diterpenes in Sage and Rosemary
Brieskom, C., and H. J. Domling. 1969. Carnosolsaure, der Wichtige Antioxidative Wirksame Inhaltsstoff des Rosmarin-und Salbeiblattes. Z. Leibensmittel Unters. Forsch. 41: 10-16
Cuvelier, M. 0E., Richard, H., and Berset, C. 1996. Antioxidative activity and phenolic composition of pilot-plant and commercial extracts of sage and rosemary. JAOCS 73: 645-652
Ford, B. A. and Hill, V. A. 2001. Chewing gum base stabilized with carnosic acid. & U.S. Pat. No. 6,231,896 B1
Lamaison, J.-L., C. Petitjean-Freytet, and A. Carnat. 1991. Lamiacées Médicinales à Propriétés Antioxydantes, source Potentielles d'acide Rosmarinique. Pharm. Acta Helv. 66: 185-188
Loliger, J. 1989. Natural Antioxidants. In: Rancidity in Food, edited by J. Allen and R. Hamilton. Elsevier Applied Science, New York, pp 105-124
Schuler, P. 1990. Natural Antioxidants Exploited Commercially. In Food Antioxidants, edited by B. Hudson. Elsevier Applied Science, New York. Pp. 99-170

Enhancement of Nisin by Emulsifiers or Chelators
U.S. Pat. No. 5,217,950
U.S. Pat. No. 5,691,301
Antimicrobial Activity of Plant Extracts: General Reviews
Nychas, G.-J. E., Skandamis, P. N. 2003. Antimicrobials from herbs and spices. In: Natural Antimicrobials for the Minimal Processing of Foods. Ed: S. Roller. CRC Press. Washington, USA.
Smid, E. J. and Gorris, L. G. M. 1999. Natural antimicrobials for food preservation. In: Handbook of Food Preservation. Ed: M. S. Rahman. Marcel Dekker Inc. New York.
Enhancement of Nisin with Lytic Enzyme (Lysozyme)
U.S. Pat. No. 5,458,876
EP 0427912
EP 0374823
Nisin Use in Food
Thomas, L. V., Clarkson, M. R., Delves-Broughton, J. 2000. Nisin. In: Natural food antimicrobials systems. pp. 463-524. CRC Press, Boca Raton, USA
Delves-Broughton, J. 1990. Nisin and its use as a food preservative. Food Technology 44: 100, 102, 104, 106, 108, 111-112, 117.
De Vuyst, De Vuyst, L., and Vandamme, E. J. 1994. Nisin, a lantibiotic produced by Lactococcus lactis subsp. lactis: properties, biosynthesis, fermentation and applications. In: Bacteriocins of lactic acid bacteria. Microbiology, Genetics and Applications. Eds: De Vuyst and Vandamme. Blackie Academic and Professional. London.
Thomas, L. V. and Delves-Broughton, J. 2001. New advances in the application of the food preservative nisin. Research Advances in Food Science 2: 11-22.
Hurst, A. 1981. Nisin. Adv. Appl. Microbiol. 27: 85-123
Hurst, A. 1983. Nisin and other inhibitory substances from lactic acid bacteria. In. Antimicrobials in Foods, eds. A. L. Branen and P. M. Davidson, pp 327-351. New York: Marcel Dekker.
Nisin Regulations
Turtell, A. and Delves-Broughton, J. 1998. International acceptance of nisin as a food preservative. Bull. Int. Dairy Fed. 329: 20-23
Bacteriocins
Naidu, A. S. (Ed.) 2000. Natural Food Antimicrobial Systems. USA: CRC Press.
Ray, B., and Miller, K. W. 2003. Bacteriocins other than nisin: the pediocin-like cystibiotics of lactic acid bacteria. In: Natural Antimicrobials for the Minimal Processing of Foods. Ed: Sibel Roller. CRC Press, USA.
Ray, B. and Daeschel, M. A. 1994. Bacteriocins of starter culture bacteria. In: Natural Antimicrobial Systems and Food Preservation. 1994. Ed: Dillon, V. M. and Board, R. G. CAB International, UK, pp 133-166.
Axelsen, L. 1998. Lactic acid bacteria: classification and physiology'. In: Salminen, S. and von Wright, A. In: Lactic Acid Bacteria. $2^{nd}$ Ed. New York, Marcel Dekker, pp 1-72.
Ray, B., Miller, K. W. and Jain, M. K 2001. Bacteriocins of lactic acid bacteria. Indian Journal of Microbiology 41: 1-21.
Hoover, D. G. 1993. Bacteriocins with potential for use in foods. In: Antimicrobials in Foods. Ed: P. M. Davidson and A. L Branen. Marcel Dekker, USA.
Wessels, S., Jelle, B., and Nes, I. F. 1998. Bacteriocins of the Lactic Acid Bacteria. Danish Toxicology Centre, Denmark.
Pediocin
Ray, B., and Miller, K. W. 2000. Pediocin. In: Natural Food Antimicrobial Systems, ed. A. S. Naidu. Pp. 525-566. USA: CRC Press All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in chemistry, biology, food science or related fields are intended to be within the scope of the following claims

The invention claimed is:

1. A method for preventing and/or inhibiting the growth of, and/or killing a micro-organism in a material, wherein:
the method comprises contacting the material with a protectant composition comprising nisin and an extract obtained from or obtainable from rosemary; and
the protectant composition comprises phenolic diterpenes in an amount of greater than 1.0 wt. % based on the protectant composition.

2. A method according to claim 1, wherein the protectant composition comprises carvacrol in an amount of less than 0.04 wt. %, based on the protectant composition.

3. A method according to claim 1, wherein the protectant composition comprises carvone in an amount of less than 0.075 wt. %, based on the protectant composition.

4. A method according to claim 1, wherein the protectant composition comprises thymol in an amount of less than 0.1 wt. %, based on the protectant composition.

5. A method according to claim 1, wherein the protectant composition comprises phenolic diterpenes in an amount of greater than 2.0 wt. %, based on the protectant composition.

6. A method according to claim 1, wherein:
the extract comprises a phenolic triterpene; and
the total amount of phenolic triterpene, based on the protectant composition, is greater than 3.5 wt. %.

7. A method according to claim 6, wherein the phenolic triterpene is selected from betulinic acid, oleanolic acid, and ursolic acid.

8. A method according to claim 1, wherein:
the extract comprises rosmarinic acid; and
the amount of rosmarinic acid, based on the protectant composition, is greater than 3.5 wt. %.

9. A method according to claim 1, wherein the nisin and the extract are present in the protectant composition in an amount to provide a microbicidal or microbiostatic synergistic effect.

10. A method according to claim 9, wherein the nisin and the extract are present in the protectant composition in an amount to provide a microbicidal synergistic effect.

11. A method according to claim 9, wherein the microbicidal or microbiostatic effect is a bactericidal or bacteriostatic effect.

12. A method according to claim 11, wherein the bactericidal or bacteriostatic effect is with respect to Gram-positive bacteria.

13. A method according to claim 1, wherein the material is a foodstuff.

14. A method according to claim 13, wherein the foodstuff is selected from raw meat, cooked meat, raw poultry products, cooked poultry products, raw seafood products, cooked seafood products, ready to eat meals, pasta sauces, pasteurised soups, mayonnaise, salad dressings, oil-in-water emulsions, margarines, low fat spreads, water-in-oil emulsions, dairy products, cheese spreads, processed cheese, dairy desserts, flavoured milks, cream, fermented milk products, cheese, butter, condensed milk products, ice cream mixes, soya products, pasteurised liquid egg, bakery products, confectionery products, fruit products, and foods with fat-based or water-containing fillings.

15. A method according to claim 1, wherein the protectant composition further comprises an emulsifier selected from polysorbates, monoglycerides, diglycerides, acetic acid esters of mono-diglycerides, tartaric acid esters of mono-diglycerides and citric acid esters of mono-diglycerides.

16. A method according to claim 1, wherein the protectant composition further comprises a chelator.

17. A method according to claim 16, wherein the chelator is selected from EDTA, citric acid, monophosphates, diphosphates, triphosphates and polyphosphates.

18. A method according to claim 1, wherein the protectant composition further comprises a lytic enzyme.

19. A method for preventing and/or inhibiting the growth of, and/or killing a micro-organism in a foodstuff, wherein:
the method comprises forming a protected foodstuff by a process comprising contacting the foodstuff with a protectant composition comprising nisin and an extract obtained from or obtainable from rosemary,
the protected foodstuff comprises a phenolic diterpene having a concentration of at least about 0.00084% w/w, and
the protected foodstuff comprises nisin at a concentration of at least about 25 IU/g.

20. A method of claim 19, wherein:
the protected foodstuff comprises a phenolic diterpene having a concentration of at least about 0.0012% w/w, and
the protected foodstuff comprises nisin at a concentration of at least about 50 IU/g.

* * * * *